United States Patent
Helson et al.

(10) Patent No.: US 9,393,198 B2
(45) Date of Patent: *Jul. 19, 2016

(54) INTRAVENOUS CURCUMIN AND DERIVATIVES FOR TREATMENT OF NEURODEGENERATIVE AND STRESS DISORDERS

(75) Inventors: Lawrence Helson, Quakertown, PA (US); Simon Chiu, London (CA)

(73) Assignee: SIGNPATH PHARMA INC., Quakertown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/052,822

(22) Filed: Mar. 21, 2011

(65) Prior Publication Data

US 2011/0229555 A1    Sep. 22, 2011

Related U.S. Application Data

(60) Provisional application No. 61/316,167, filed on Mar. 22, 2010, provisional application No. 61/412,241, filed on Nov. 10, 2010.

(51) Int. Cl.
| | | |
|---|---|---|
| *A61K 9/127* | (2006.01) | |
| *A61K 31/12* | (2006.01) | |
| *A61K 47/48* | (2006.01) | |

(52) U.S. Cl.
CPC ............... *A61K 9/127* (2013.01); *A61K 31/12* (2013.01); *A61K 47/482* (2013.01)

(58) Field of Classification Search
CPC .......... A61K 2300/00; A61K 36/9066; A61K 9/127; A61K 45/06; A61K 9/00
See application file for complete search history.

(56) References Cited

U.S. PATENT DOCUMENTS

| | | |
|---|---|---|
| 4,812,312 A | 3/1989 | Lopez-Berestein et al. |
| 5,023,087 A | 6/1991 | Yau-Young |
| 5,679,864 A | 10/1997 | Krackov et al. |
| 6,143,276 A | 11/2000 | Unger |
| 6,787,132 B1 | 9/2004 | Gabizon et al. |
| 7,060,733 B2 | 6/2006 | Pandol et al. |
| 7,067,159 B2 | 6/2006 | Katz et al. |
| 7,507,864 B2 | 3/2009 | Miller et al. |
| 7,674,820 B2 | 3/2010 | Fedida et al. |
| 7,723,515 B1 | 5/2010 | DiMauro |
| 7,871,609 B2 | 1/2011 | Ziff et al. |
| 8,062,663 B2 | 11/2011 | Wang et al. |
| 8,153,172 B2 | 4/2012 | Antony |
| 8,202,839 B1 | 6/2012 | Sung |
| 8,207,219 B2 | 6/2012 | Fedida et al. |
| 8,747,890 B2 | 6/2014 | Helson |
| 8,753,674 B2 | 6/2014 | Helson |
| 9,138,411 B2 | 9/2015 | Ranjan et al. |
| 2001/0051184 A1 | 12/2001 | Heng |
| 2002/0048598 A1 | 4/2002 | Malik |
| 2005/0233970 A1 | 10/2005 | Garnick |
| 2006/0067998 A1 | 3/2006 | Kurzrock et al. |
| 2006/0147512 A1 | 7/2006 | Sabin |
| 2007/0048284 A1 | 3/2007 | Donahue et al. |
| 2008/0075671 A1 | 3/2008 | Di Mauro |
| 2008/0103213 A1 | 5/2008 | Kurzrock et al. |
| 2008/0107749 A1 | 5/2008 | Maitra et al. |
| 2008/0138400 A1 | 6/2008 | Kurzrock et al. |
| 2008/0253961 A1 | 10/2008 | Braden et al. |
| 2008/0255464 A1 | 10/2008 | Vincent |
| 2009/0143433 A1 | 6/2009 | Hendrix |
| 2009/0246770 A1 | 10/2009 | Levy |
| 2009/0317387 A1 | 12/2009 | Paton et al. |
| 2009/0324703 A1 | 12/2009 | Frautschy et al. |
| 2010/0004549 A1 | 1/2010 | Kohls et al. |
| 2010/0048957 A1* | 2/2010 | Kim ............................ 568/324 |
| 2010/0093873 A1 | 4/2010 | Goldfischer |
| 2010/0120890 A1 | 5/2010 | Fedida |
| 2010/0151000 A1 | 6/2010 | Davies et al. |
| 2010/0179103 A1 | 7/2010 | Desai |
| 2010/0239552 A1 | 9/2010 | Mayoux et al. |
| 2010/0240581 A1 | 9/2010 | Tortoriello et al. |
| 2011/0117186 A1 | 5/2011 | Helson |
| 2011/0287085 A1 | 11/2011 | Kurzrock et al. |
| 2012/0003177 A1 | 1/2012 | Murdoch et al. |

(Continued)

FOREIGN PATENT DOCUMENTS

| | | |
|---|---|---|
| CA | 2584279 A1 | 4/2005 |
| JP | H10-191927 A | 7/2010 |

(Continued)

OTHER PUBLICATIONS

Fahn. Medical Treatment of Parkinson's Disease. Journal of Neurology, 1998. 245 [Supplement 3]: P15-P24.*
Marino et al. Sertaline in the Treatment of Depressive Disorders in Patients With Parkinson's Disease. Neurological Sciences, 2008. 29: 391-395.*
Harish et al Bioconjugates of Curcumin Display Improved Protection Against Glutathione Depletion Mediated Oxidative Stress in a Dopaminergic Neuronal Cell Line: Implications for Parkinson's Disease. Bioorganic & Medicinal Chemistry, 2010. 18:2631-2638. Available online Feb. 20, 2010.*
Abel, Ted., et al., "Epigenetic Targets of HDAC Inhibition in Neurodegenerative and Psychiatric Disorders," Current Opinion in Pharmacology, (2008), vol. 8, pp. 57-64.
Anderson, P., et al., "The Hippocampus Book," Oxford University Press, 2006, 102 pages.
Ataie, Amin, et al., "Neuroprotective Effects of the Polyphenolic Antioxidant Agnet, Curcumin, Against Homocysteine-Induced Cognitive Impairment and Oxidative Stress in the Rat," Pharmacology, Biochemistry and Behavior, (2010), vol. 96, pp. 378-385.
Bala, Kiran, et al., "Neuroprotective and Anti-Aging Effects of Curcumin in Aged Rat Brain Regions," Biogerontology, (2006), vol. 7, pp. 81-89.

(Continued)

*Primary Examiner* — Maria Leavitt
*Assistant Examiner* — Kimberly A Aron
(74) *Attorney, Agent, or Firm* — Edwin S. Flores; Chainey P. Singleton; Chalker Flores, LLP

(57) ABSTRACT

Liposomal formulations and polymer conjugates of curcumin, curcumin analogs and derivatives thereof for parenteral administration are disclosed herein. The formulations are effective in the treatment of progressive supranuclear palsy, Alzheimer's disease (AD), Parkinson's disease (PD), Tauopathies or stress disorders including Post Traumatic Stress Disorder (PTSD). Curcumin crosses the blood brain barrier, localizes in the hippocampus and striata, prevents stress-induced neuronal cell damage, and stimulates neurogenesis and remediation of damaged neural circuits.

15 Claims, 1 Drawing Sheet

(56) References Cited

U.S. PATENT DOCUMENTS

| | | |
|---|---|---|
| 2012/0021036 A1 | 1/2012 | Majeti et al. |
| 2012/0058208 A1 | 3/2012 | Jacob |
| 2012/0237590 A1 | 9/2012 | Helson |
| 2012/0308643 A1 | 12/2012 | Helson |
| 2013/0310351 A1 | 11/2013 | Milan et al. |
| 2013/0337488 A1 | 12/2013 | Helson |

FOREIGN PATENT DOCUMENTS

| | | | |
|---|---|---|---|
| WO | 0070949 A1 | | 11/2000 |
| WO | 2004047717 A2 | | 6/2004 |
| WO | 2004080396 A2 | | 9/2004 |
| WO | WO 2006061101 A2 | * | 6/2006 |
| WO | 2007006028 A2 | | 5/2007 |
| WO | 2007103435 A2 | | 9/2007 |
| WO | 2008045534 A2 | | 4/2008 |
| WO | 2008063513 A2 | | 5/2008 |
| WO | 2008128123 A1 | | 10/2008 |
| WO | WO 2009051837 A2 | * | 4/2009 |
| WO | 2010009186 A1 | | 1/2010 |
| WO | 2010033692 A1 | | 3/2010 |
| WO | 2010057332 | | 5/2010 |
| WO | 2011063178 A1 | | 5/2011 |
| WO | 2011001351 | | 6/2011 |
| WO | 2011119588 | | 9/2011 |
| WO | 2012125830 A2 | | 9/2012 |
| WO | 2012167212 A2 | | 12/2012 |
| WO | 2013188767 A1 | | 12/2013 |

OTHER PUBLICATIONS

Bisht, Savita, et al., "Polymeric Nanoparticle-Encapsulated Curcumin ("nanocurcumin"): A Novel Strategy for Human Cancer Therapy," Journal of Nanobiotechnology, (2007), vol. 5, No. 3, 18 pages.

Garcia-Alloza, M., et al., "Curcumin Labels Amyloid Pathology in Vivo, Distrupts Existing Plaques, and Partially Restroes distorterneurites in an Alzheimer Mouse Model," Journal of Neurochemistry, (2007), vol. 102, pp. 1095-1104.

International Search Report and Written Opinion for PCT/US2011/029393, dated Jun. 23, 2011, 7 pages.

Kessler, Ronald C., et al., "Posttraumatic Stress Disorder in the national Comorbidity Survey," Archives of General Psychiatry, vol. 52, No. 12, pp. 1049-1060, 1995.

Kim, So Jung, et al., "Curumin Stimulates Proliferation of Embryonic Neural Progenitor Cells and Neurogenesis in the Adult Hippocampus," The Journal of Biological Chemistry, May 23, 2008, vol. 283, No. 21, pp. 14497-14505.

Li, Yu-Cheng, et al., "Antidepressant-Like Effects of Curcumin on Serotonergic Receptor-Coupled Ac-cAMP Pathway in Chronic Unpredictable Mild Stress of Rats," Progress in Neuro-Psychophamacoloby & Biological Psychiatry, (2009), vol. 33, pp. 435-449.

Li, Lan, et al., "Liposome-Encapsulated Curcumin," Cancer, Sep. 15, 2005, vol. 104, No. 6, pp. 1322-1331.

Mukerjee, Anindita, et al., "Formulation, Characterization and Evaluation of Curcumin-Loaded PLGA Nanospheres for Cancer Therapy," Anticancer Research, (2009), vol. 29, pp. 3867-3876.

Pitman, Roger K., et al., "Conceptually Driven Pharmacologic Approaches to Acute Trauma," CNS Spectrums, Feb. 2005, vol. 10, No. 2, pp. 99-106.

Rosi, S., et al., "Chemokine Receptor 5 Antagonist d-Ala-Peptide T-Amide Reduces Microglia and Astrocyte Activation Within the Hippocampus in a Neuroinflammatory Rat Model of Alzheimer's Disease," Neuroscience, (2005), vol. 134, pp. 671-676.

Rui, Pan, et al., "Curcumin Improves Learning and Memory Ability and its Neuroprotective Mechanism in Mice," Chin. Med. J., (2008), vol. 121, No. 9, pp. 832-839.

Rusinek, Henry, et al., "Hippocampal Blood Flow in Normal Aging Measured with Arterial Spin Lavelin at 3T," Magnetic Resonance in Medicine, (2011), 65:128-137.

Segman, RH., et al., "Association Between the Dopamine Transporter Gene and Posttraumatic Stress Disorder," Molecular Psychiatry, (2002), vol. 7, pp. 903-907.

Segman, RH., et al., "Peripheral Blood Mononuclear Cell Gene Expression Profiles Identify Emergent Post-Traumatic Stress Disorder Among Trauma Survivors," Molecular Psychiatry, (2005), vol. 10, pp. 500-513.

Stein, Murray B., et al., "Genetic and Environmental Influences on Trauma Exposure and Posttraumatic Stress Disorder Symptoms: A Twin Study," Am. J. Psychiatry, Oct. 2002, vol. 159, No. 10, pp. 1675-1681.

Xu, Ying, et al., "Curcumin Reverses Impaired Hippocampal Neurogenesis and Increases Serotonin Receptor 1A mRNA and Brain-Derived Neurotrophic Factor Expression in Chronically Stressed Rats," Brain Research, (2007), 1162, pp. 9-18.

Aggarwal, et al., "The Molecular Targets and Therapeutic Uses of Curcumin in Health and Disease," (2006), Springer, 515 pages.

Bentzen, Peter J., et al., "Curcumin Induced Suicidal Erythrocyte Death," Cellular Physiology and Biochemistry, (2007), 19:153-164.

Everett, Peter C., et al., "Preclinical Assessment of Curcumin as a Potential Therapy for B-CLL," American Journal of Hematology, (2006), 8 pages.

Logan-Smith, Melanie J., et al., "Curcumin, a Molecule that Inhibits the Ca2+ -ATPase of Sarcoplasmic Reticulum but Increases the Rate of Accumulation of Ca2+," The Journal of Biological Chemistry, (2001), vol. 276, No. 50, pp. 46905-46911.

Mach, Claire M., et al., "Determination of Minimum Effective Dose and Optimal Dosing Schedule for Liposomal Curcumin in a Xenograft Human Pancreatic Cancer Model," (2009), Anticancer Research, 29:1895-1900.

Smith, Judith A., et al., "Abstract A29: Development of Liiposomal Curcumin as a New Potential Anticancer Agent," Molecular Cancer Therapeutics, Dec. 2009, vol. 8, Issue 12, Supplement 1, 1 page.

Tonnesen, Hanne, H., et al, "Studies on curcumin and curcuminoids: XXV. Inhibition of primaquine-induced lysis of human red blood cells by curcumin," International Journal of Pharmaceutics 110 (1994) 161-167.

Extended European Search Report and Europeean Search Opinion for EPO 10832224.9 dated Feb. 26, 2013.

Extended and Supplemental European Search Report for EPO 12792560.0 dated Oct. 30, 2014, 11 pages.

Mayer, Lawrence D., et al., "Intravenous Pretreatment with Empty pH Liposomes Alters the Pharmacokinetics and Toxicity of Doxorubicin through In Vivo Active Drug Encapsulation," Journal of Pharmaceutical Sciences, vol. 88, No. 1, Nov. 25, 1998, pp. 96-102.

Nousiainen, T., et al., "QT dispersion and late potentials during doxorubicin therapy for non-Hodgkin's lymphoma," Journal of Internal Medicine, 245, 1999, pp. 359-364.

Schena, Francesco P., et al., "Pathogenetic Mechanisms of Diabetic Nephropathy," J. Am. Soc. Nephrol., (2005), 16: S30-S33.

International Search Report and Written Opinion for PCT/US2014/071246, dated Mar. 27, 2015, 14 pages.

International Search Report and Written Opinion for PCT/US2013/057744 dated Dec. 12, 2013, 14 pages.

Anderson, Corey, et al., "Most LQT2 Mutations Reduce Kv11.1 (hERG) Current by a Class 2 (Trafficking-Deficient) Mechanism," Circuilation, Nov. 11, 2005, pp. 365-373.

Crouch, et al., "Clinical Relevance and Management of Drug-Related QT Interval Prolongation," Pharmacotherapy, Nov. 7, 2003, vol. 23:7, pp. 881-908.

Doherty, K, et al., "Multi-parameter in vitro toxicity testing of crizotinib, sunitinib, erlotinib, and nilotinib in human cardiomyocytes," Toxicoloty and Applied Pharmacology, Apr. 28, 2003, vol. 272, pp. 245-255.

FDA Pharmacology Review of Xalkori (crizotinib), IND No. 202570, 2011a, www.accessdata.fda.gov/drugsatfda__docs/nda/2011/202570Orig1s000PharmR.pdf (accessed Oct. 9, 2013).

FDA Pharmacology of Tasigna® (nilotinib), IND No. 22-068, 2007a, www.accessdata.fda.gov/drugsatfda__docs/nda/2007/022068s000__PharmR__P1.pdf and www.accessdata.fda.gov/drugsatfda__docs/nda/2007/022068s000__MedR__P2.pdf, (accessed Oct. 25, 2013).

(56) References Cited

OTHER PUBLICATIONS

Helson, et al., "Liposome mitigation of curcumin inhibition of cardiac potassium delayed-rectifier current," Journal of Receptor, Ligand and Channel Research, Nov. 15, 2012, vol. 5, pp. 108.
Kim, K-P., et al., "Nilotinib in Patients with GIST who failed imatinib and sunitinib: importance of prior surgery on drug bioavailability," Jul. 12, 2010, Cancer Chemother. Pharmacol., vol. 68, pp. 285-291.
Layton, D, et al., "Prolongation of the QT interval and cardiac arrhythmias associated with cisapride: limitations of the pharmacoepidemiological studies conducted and proposals for the future," Pharmacoepidemiol Drug Saf., 12(1), Nov. 13, 2002, pp. 31-40.
Lee, et al., "Electrophysiological Effects of the Anti-Cancer Drug Lapatinib on Cardiac Repolarization," Basic & Clinical Pharmocology & Toxicology, vol. 107, Dec. 21, 2009, pp. 614-618.
Mehta, RT, et al., "Formulation, toxicity, and antifungal activity in vitro of liposomal-encapsulated nystatin as therapeutic agent for systemic candidiasis," Antimicrob Agents Chemother., 31(12), Dec. 1987, pp. 1897-1900.
Moha, H, et al., "Curcumin blocks the recombinant human cardiac KCNQ 1/KCNE 1 channels (IKs) stably expressed in HEK 293 cells," Abstract of 12th Annual Meeting of the French Society of Pharmacology and Therapeutics, Fund. & Clin. Pharma., vol. 22:1, Jun. 2008.
Mosse, et al., "Safety and activity of crizotinib for pediatric patients with refractory solid tumours of anaplastic large-cell lymphoma: a Children's Oncology Group phase 1 consortium study," Lancet Oncol., May 2013, vol. 14(6), pp. 472-480.
Murphy, Eric, A., et al., "Targeted Nanogels: A Versatile Platform for Drug Delivery to Tumors," Molecular Cancer Therapeutics, Apr. 25, 2011; 10:972-982.
Nam, et al., "Curcumin-Loaded PLGA Nanoparticles Coating onto Metal Stent by Electrophoretic Deposition Techniques," Bull. Korean Chem. Soc., Jan. 2007, vol. 28, No. 3, pp. 397-402.
Naseem, et al., "Bupivacaine Extended Release Lipsome Injection Does not Prolong Qtc Interval in a Thorough QT/QTc Study in Healthy Volunteers," Journal of Clin. Pharma., 2012, vol. 52, pp. 1441-1447.
Quan, Xiao-Qing, et al., "Increasing Gap Junction Coupling Reduces Transmural Dispersion of Repolarization and Prevents Torsade de Pointes in Rabbit LQT3 Model," J. Cardiovasc. Electrophysiol., vol. 18, Nov. 2007, pp. 1184-1189.
Rajamani, S., et al., "Drug-induced long QT syndrome: hERG K+ channel block and disruption of protein trafficking by fluoxetine and norfluoxetine," British Journal of Pharmacology, Sep. 11, 2006, vol. 149, pp. 481-489.
Ranjan, A. P., et al, "Efficacy of Liposomal Curcumin in a Human Pancreatic Tumor Xenograft Model: Inhibition of Tumor Growth and Angiogenesis," Anticancer Research, vol. 33, Jul. 26, 2013, pp. 3603-3610.
Ravindran, J., et al., "Curcumin and Cancer Cells: How Many Ways Can Curry Kill Tumor Cells Selectively?," The AAPS Journal, vol. 11, No. 3, Jul. 10, 2009, pp. 495-510.
Shah, et al., "Cardiovascular Safety of Tyrosine Kinase Inhibitors: With a Special Focus on Cardiac Repolarisation (QT Interval)," Drug Saf., Apr. 26, 2013, vol. 36, pp. 295-316.
Shimizu, Wataru, et al., "Sodium Channel Block with Mexiletine is Effective in Reducing Dispersion of Repolarization and Preventing Torsade de Pointes in LQT2 and LQT3 Models of the Long-QT Syndrome," vol. 96, Apr. 28, 1997, pp. 2038-2047.
Stansfeld, Phillip, J., et al., "Drug Block of the hERG Potassium Channel: Insight From Modeling," PROTEINS: Structure, Function and Bioinformatics, Apr. 19, 2007, 68:568-580.
TASIGNA Package insert, Novartis Pharmaceuticals, Revised Sep. 2013.
U.S. Department of Health and Human Services, "Guidance for Industry, S7B Nonclinical Evaluation of the Potential for Delayed Ventricular Repolarization (QT Interval Prolongation) by Human Pharmaceuticals," Oct. 2005, pp. 1-13.

Van De Water, et al., "An Improved Method to Correct the QT Interval of the Electrocardiogram for Changes in Heart Rate," Journal of Pharmacological Methods, Apr. 1989, vol. 22, pp. 207-217.
Witchel, "Drug-induced hERG Block and Long QT Syndrome," Cardiovascular Therapeutics, 2011, vol. 29, pp. 251-259.
Xalkori Package insert, Pfizer Laboratories, revised Feb. 2013, 10 pages.
Yang, Ping, et al., "Allelic Variants in Long-QT Disease Genese in Patients with Drug-Associated Rosades de Pointes," Circulation, Apr. 23, 2002, pp. 1943-1948.
Yap, Y. G., et al., "Drug Induced QT Prolongation and Torsades de Pointes," Heart, vol. 89, Nov. 2003, pp. 1363-1372.
Zachariae, U., et al., "Side chain flexabilities in the human ether-a-go-go related potassium channel (hERG) together with matched-pair binding studies suggest a new binding mode for channel blockers," J. Med. Chem., vol. 52 (14),Jan. 2, 2009, pp. 4266-4276.
Zhang, L., et al., "Self-Assembled Lipid-Polymer Hybrid Nanoparticles: A Robust Drug Delivery Platform," ACS Nano, vol. 2:8, Jul. 23, 2008, pp. 1696-1702.
Zhou, L., et al., "Nilotinib for Imatinib-Resistant or -Intolerant Chronic Myeloid Leukemia in Chronic Phase, Accelerated Phase, or Blast Crisis: A Single- and Multiple-Dose, Open-Label Pharmacokinetic Study in Chinese Patients," Clinical Therapeutics, vol. 31:7, Jul. 2009, pp. 1568-1575.
Zhou, et al., "Correction of Defectrive Protein Trafficking of a Mutant HERG Potassium Channel in Human Long QT Syndrome," The Journal of Biological Chemistry, vol. 274:44, Oct. 29, 1999, pp. 31123-31126.
International Search Report and Written Opinion for PCT/US2010/057332, dated Aug. 2, 2011, 12 pages.
International Search Report and Written Opinion for PCT/US2011/029393, dated Jun. 23, 2011, 17 pages.
International Search Report and Written Opinion for PCT/US2012/029230, dated Sep. 21, 2012, 14 pages.
International Search Report and Written Opinion for PCT/US2012/040637, dated Dec. 12, 2012, 13 pages.
International Search Report and Written Opinion for PCT/US2013/045898, dated Sep. 6, 2013, 12 pages.
Arbiser, Jack L., et al., "Curcumin is an In Vivo Inhibitor of Angiogenesis," Moledular Medicine, (1998), 4:376-383.
Bisht, Savita, et al., "Systemic Administration of Polymeric Nanoparticle-Encapsulated Curcumin (NanoCurcTM) Blocks Tumor Growth and Metastases in Preclinical Models of Pancreatic Cancer," Mol. Cancer Ther., (Aug. 2010), 9(8):2255-2264.
Blomgren, Kerstin, et al., "Obesity and Treatment of Diabetes with Glyburide may Both be Risk Factors for Acute Pancreatitis," Diabetes Care, (2002), 25:298-302.
Brownlee, Michael, "Biochemistry and Molecular Cell Biology of Diabetic Complications," Nature, Dec. 13, 2001, vol. 414, pp. 813-820.
Chao, Chun C., et al., "Glia: The Not So Innocent Bystanders," Journal of NeuroVirology, (1996), 2:234-239.
Chen, Shali, et al., "High glucose-induced, endothelin-dependent fibronectin synthesis is mediated via NF- kB and AP-1," Am J. Physiol. Cell Physiol., Sep. 18, 2002, 284:C263-C272.
Chen, et al., "An in vitro study of liposomal curcumin: stability, toxicity and biological activity in human lymphocytes and epstein-barr virus-transformed human B-cells," International Journal of Pharmaceutics, Jan. 2009, vol. 366, Issue 1-2, pp. 133-139.
Chiu, Jane, et al., "Curcumin Prevents Diabetes-Associated Abnormalities in the Kidneys by Inhibiting p300 and Nuclear Factor-kB," Nutrition, (2009), 25:964-972.
Compton, SJ, et al., "Genetically Defined Therapy of Inherited Long-QT Syndrome. Correction of Abnormal Repolarization by Potassium," Circulation, 1996; 94:1018-1022.
Crack, Peter J., et al., "Glutathione Peroxidase-1 Contributes to the Neuroprotection Seen in the Superoxide Dismutase-1 Transgenic Mouse in Response to Ischemia/Reperfusion Injury," Journal of Cerebral Blood Flow and Metabolism, (2003), vol. 23, No. 1, pp. 19-22.
D'Amico, Michele, et al., "Long-Term Inhibition of Dipeptidyl Peptidase-4 in Alzheimer's Prone Mice," Experimental Gerontology 45,3, (2010), 24 pages.

(56) References Cited

OTHER PUBLICATIONS

Djeddi, D, et al., "A: Effect of Domperidone on QT Interval in Neonates," J Pediatrics, 2008; 153(5):596-598.

Ducroq, J, et al., "Printemps R, Le Grand M.: Additive Effects Ziprasidone and D,L-Sotalol on the Action Potential in Rabbit Purkinje Fibers and on the hERG Potassium Current," J.Pharmacol. Toxicol Methods, 2005; 52:115-122.

Etheridge, SP, et al., "A New Oral Therapy for Long QT Syndrome: Long Term Oral Potassium Improves Repolarization in Patients with hERG Mutations," J Am Coll Cardiol, 2003; 42:1777-1782.

Fauchier, L, et al.,"JP: Effect of Verapamil on QT Interval Dynamicity," Am J Cardiol., 1999; 83(5):807-808 A10-1.

Fowler, NO, et al., "Electrocardiographic Changes and Cardiac Arrhythmias in Patients Receiving Psychotropic Drugs," Am J Cardiol, 1976; 37(2):223-230.

Gukovsky, Ilya, et al., "Curcumin Ameliorates Ethanol and Nonethanol Experimental Pancreatitis," Am. J. Physiol. Gastrointest. Liver Physiol., (2003), 284:G85-G95.

Helson, et al., "Infusion pharmacokinetics of lipocure (liposomal curcumin) and its metabolite tetrahydrocurcumin in beagle dogs," Anticancer Research, Oct. 2012, vol. 32, No. 10, pp. 4365-4370.

Hernandez-Fonseca, Juan P., et al., "Structural and Ultrastructural Analysis of Cerebral Cortex, Cerebellum, and Hypothalamus from Diabetic Rats," Experimental Diabetes Research Oct. 1, 2009: 2009: 329632.

Ireson, Christopher, et al., "Characterization of Metabolites of the Chemopreventive Agent Curcumin in Human and Rat Hepatocytes and in the Rat in Vivo, and Evaluation of Their Ability to Inhibit Phorbol Ester-induced Prostaglandin E2 Production," Cancer Research 61:1058-1064, 2001, pp. 1059-1062.

Jacob, Asha, et al., "Mechanism of the Anti-Inflammatory Effect of Curcumin: PPAR-y Activation," Hindawi Publishing Corporation, PPAR Research, (2007), Article ID 89369, 5 pages.

Jervell, A, et al., "Congenital Deaf-Mutism, Functional Heart Disease with Prolongation of the QT Interval and Sudden Death," Am Heart J., 1957; 54(1):59-68.

Kang, J, et al., "Discovery of a Small Molecule Activator of the Human Ether-a-go-go—Related Gene(HERG) Cardiac K+ Channel," Mol Pharmacol, 2005(3); 67:827-836.

Katchman, AN, et al., "Comparative Evaluation of HERG Currents and QT Intervals Following Challenge with Suspected Torsadogenic and Nontorsdogenic Drugs," J Pharmacol Exp Ther., 2006; 316(3):1098-1106.

Koehler, Jacqueline A., et al., "Glucagon-Like Peptide-1 Receptor Activation Modulates Pancreatitis-Associated Gene Expression Bud Does Not Modify the Susceptibility to Experimental Pancreatitis in Mice," Diabetes, Sep. 2009, vol. 58, pp. 2148-2161.

Kourelis, Taxiarchis V., et al., "Metformin and Cancer: New Applications for an Old Drug," Med. Oncol., Feb. 8, 2011, 14 pages.

Kowluru, Renu A., et al., "Effects of Curcumin on Retinal Oxidative Stress and Inflammation in Diabetes," Nutrition & Metabolism, Apr. 16, 2007, 8 pages.

Kumar, T. Peeyush, et al., "Curcumin Modulates Dopaminergic Receptor, CREB and Phospholipase C Gene Expression in the Cerebral Cortex and Cerebellum of Streptozotocin Induced Diabetic Rats," Journal of Biomedical Science, (2010), 2:43, 11 pages.

Lamont, Benjamin J., et al., "Differential Antidiabetic Efficacy of Incretin Agonists Versus DPP-4 Inhibition in High Fat-Fed Mice," Diabetes, Jan. 2008, vol. 57, pp. 190-198.

Leung, et al., "Effective stablization of curcumin by association to plasma proteins: human serum albumin and fibronogen," Langmuir, 2009, vol. 25, Issue 10, pp. 5773-5777.

Lim, Kah Jing, et al., "A Polymeric Nanoparticle Formulation of Curcumin Inhibits Growth, Clonogenicity and Stem-Like Fraction in Malignant Brain Tumors," Cancer Biology & Therapy, Mar. 1, 2011, 11:5, pp. 464-473.

Maciel, NR, et al., "Reduced Cardiovascular Alterations of Tarter Emetic Administered in Long-Circulating Liposomes in Rats," Toxicology Letters, 2010; 199(3)234-238.

Matsushita, Yuichi, et al., "Activation of Peroxisome Proliferator-Activated Receptor d Inhibits Streptozotocin-Induced Diabetic Nephropathy Through Anti-Inflammatory Mechanisms in Mice," Diabetes, Mar. 2011, vol. 60, pp. 960-968.

Narala, Venkata R., et al., "Curcumin is not a Ligand for Peroxisome Proliferator-Activated Receptor-Y," Gene Therm. Mol. Biol., Apr. 1, 2009, 13(1):20-25.

Olansky, Leann, "Do Incretin-Based Therapies Cause Acute Pancreatitis?" Journal of Diabetes Science and Technology, Jan. 2010, vol. 4, Issue 1, pp. 228-229.

Riyouji, Takagaki, et al., "Method for Stablizing Curcuminoid and Stablized Curcuminoid Compound," English Abstract, Japanese Patent Application Publication No. JP 10191927 A, p. 1-11, specif pp. 4-5.

Roberts, A.N., et al., "Molecular and Functional Characterization of Amylin, a Peptide Associated with Type 2 Diabetes Mellitus," Proc. Natl. Acad. Sci. USA, Dec. 1989, vol. 86, pp. 9662-9666.

Shimizu, Wataru, et al. "Effects of a K+ Channel Opener to Reduce Transmural Dispersion of Repolarization and Prevent Torsade de Pointes in LQT1, LQT2, and LQT3 Models of the Long-QT Syndrome," Circulation, 2000, 102:706-712.

Singh, Sonal, et al., "Long-Term Risk of Cardovascular Events with Rosiglitazone," JAMA, Sep. 12, 2007, vol. 298, No. 10, pp. 1189-1195.

Verma, Richa, et al., "Structural and functional changes in a syntheitic S5 segment of KvLQT1 channel as a result of a conserved amino acid substitution that occurs in LQT1 syndrome of human," Biochimica et Biophysica Acta, 1798, Jan. 2010, pp. 461-470.

Vidal, Alessandra Teixeira, et al., "Prolonged cardioprotective effect of pyridostigmine encapsulated in liposomes," Life Sciences, vol. 86, 2010, pp. 17-23.

Wang, Timothy C., et al., "Pancreatic Gastrin Stimulates Islet Differentiation of Transforming Growth Factor a-Induced Ductular Precursor Cells," The Journal of Clinical Investigation, Inc., Sep. 1993, vol. 92, pp. 1349-1356.

Wesley, Umadevi V., et al., "Role for Dipeptidyl Peptidase IV in Tumor Suppression of Human Non Small Cell Lung Carcinoma Cells," Int. J. Cancer, (2004), 109:855-866.

Wesley, Umadevi V., et al., "Dipeptidyl Peptidase Inhibits Malignant Phenotype of Prostate Cancer Cells by Blocking Basic Fibroblast Growth Factor Signaling Pathway," Cancer Res., (2005), a65:1325-1334.

Whitten, Kenneth, et al., "The Common Ion Effect and Buffer Solutions," Chapter 19-1, Chemistry [online] Copyright 2013, Cengage Learning, Independence, KY.

Wu, Aiguo, et al., "Brain and Spinal Cord Interaction: A Dietary Curcumin Derivative Counteracts Locomotor and Cognitive Deficits After Brain Trauma," Neurohabil Neural Repair, May 2011, 25(4):332-342.

Xie, Y., et al., "Combinative method using HPLC quantitative and qualitative analyses for quality consistency assessment of a herbal medicinal preparation," Journal of Pharmaceutical and Biomedical Analysis, vol. 43:204-212, pp. 205-208.

Extended and Supplemental European Search Report for EPO 11760055.1 dated Jun. 13, 2014, 7 pages.

Begun, A.N., et al., "Curcumin Structure-Function, Bioavailibility, and Efficacy in Models of Neuroinflammation and Alzheimer's Disease," The Journal of Pharmacoloby and Experimental Therapeutics, vol. 326:1, Apr. 15, 2008, pp. 196-208.

Grama, C.N., et al., "Poly(lactide-glycolide) nanoparticles for peroral delivery of bioactives," Current Opinion in Colloid and Interface Science, London, GB, vol. 16, No. 3, Nov. 24, 2010, pp. 238-245.

Konwarh, R., et al., "Poly(ethylene glycol)-magnetic nanoparticles-curcumin trio: Directed morphogenesis and synergistic free-radical scavenging," Colloids and Surfaces B: Biointerfaces, vol. 81, Aug. 7, 2010, pp. 578-586.

Mishra, S., et al., "The effect of curcumin (turmeric) on Alzheimer's disease: An overview," Annals of Indian Academy of Neurology, vol. 11:1, 2008, pp. 13-19.

Rajeswari, A., et al., "Inhibition of monoamine oxidase-B by the polyphenolic compound, curcumin and its metabolite

(56) References Cited

OTHER PUBLICATIONS tetrahydrocurcumin, in a model of Parkinson's disease induced by MPTP neurodegeneration in mice," Inflammopharmacology, vol. 16, 2008, pp. 96-99.

Shaikh, J., et al, "Nanoparticle encapsulation improves oral bioavailability of curcumin by at least 9-fold when compared to curcumin administered with piperine as absorption enhancer," European Journal of Pharmaceutical Sciences, Elsevier, Amsterdam, NL, vol. 37, No. 3-4, Jun. 28, 2009, pp. 223-230.

Sun, M., et al., "Enhancement of transport of curcumin to brain in mice by poly(n-butylcyanoacrylate) nanoparticle," J. Nanopart Res., vol. 12, 2010, pp. 3111-3122.

Extended European Search Report and Europeean Search Opinion for EPO 12757689.0 dated Oct. 22, 2014, 7 pages.

International Search Report and Written Opinion for PCT/US2015/034078, dated Aug. 31, 2015, 17 pages.

Wang, Jingxiong, et al., "Phospholipid metabolite 1-palmitoyl-lysophosphatidylcholine enhances human ether-a-go-go-related gene (HERG) K+ channel function", Circulation, 2001, vol. 104, No. 22, pp. 2645-2648.

* cited by examiner

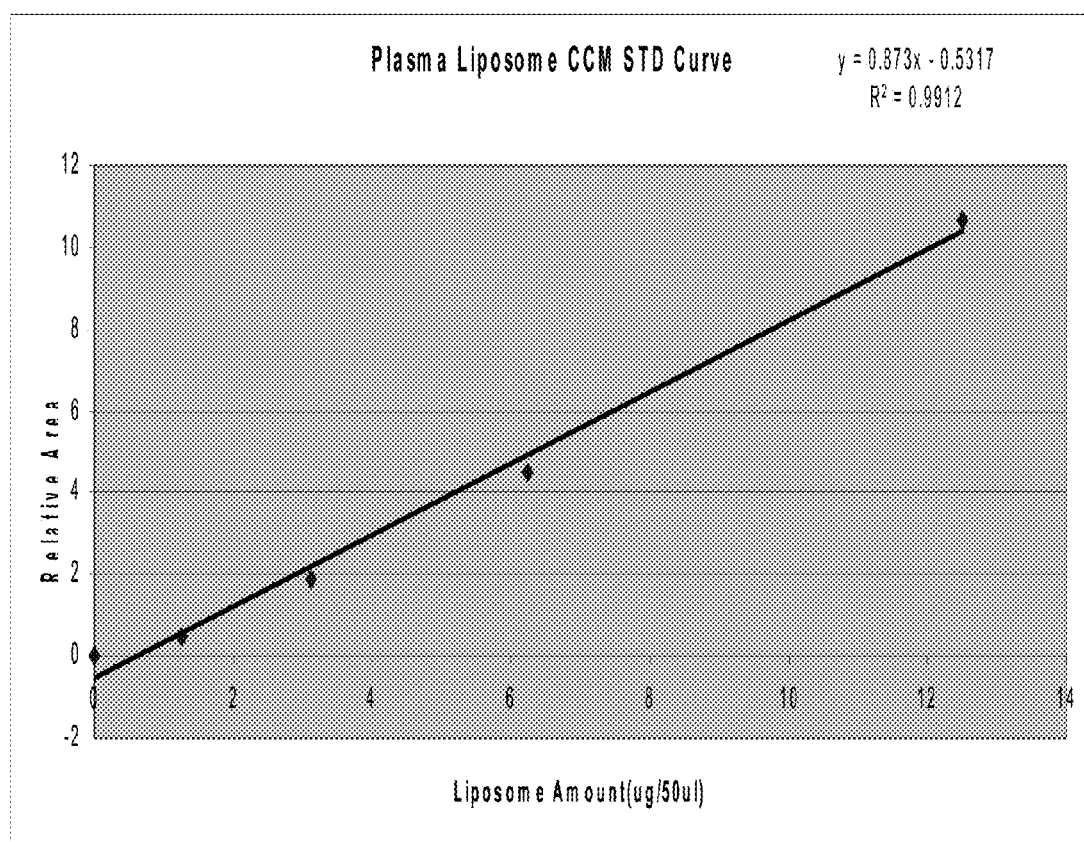

INTRAVENOUS CURCUMIN AND DERIVATIVES FOR TREATMENT OF NEURODEGENERATIVE AND STRESS DISORDERS

CROSS-REFERENCE TO RELATED APPLICATIONS

This patent application is a non-provisional application of U.S. provisional patent application No. 61/316,167 filed on Mar. 22, 2010 entitled "Intravenous Curcumin and Derivatives for Treatment of Post Traumatic Stress Disorder (PTSD)" and U.S. provisional patent application No. 61/412, 241 filed on Nov. 10, 2010 entitled "Intravenous Curcumin and Derivatives for Treatment of Neurodegenerative and Stress Disorders" which are hereby incorporated by reference in their entirety.

TECHNICAL FIELD OF THE INVENTION

The present invention relates in general to the field of managing and treating stress related disorders, and more particularly to the use of intravenous formulations comprising liposomal curcumin for the treatment of neurodegenerative and stress disorders including post traumatic stress disorders (PTSD).

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with the use of compositions comprising curcumin and analogues and derivatives thereof for the treatment of neurological, neurodegenerative and other disorders.

U.S. Patent Application No. 20080033055 (Miller and Mitchell, 2008) relates to improved methods for achieving the synthesis of 1,7-diaryl-1,6-heptadiene-3,5-diones, and in particular curcumin and its analogues. The invention also relates to the use of such synthesized products in the treatment of Alzheimer's Disease and other diseases.

U.S. Patent Application No. 20090143433 (Hendrix, 2009) discloses formulations for the prevention and treatment of neurological diseases and cognitive deficiencies, i.e., Alzheimer's Disease (AD), Parkinson's Disease, amyotrophic lateral sclerosis, mild cognitive impairment and other types of dementia, comprise therapeutically effective amounts of curcumin, piperine, epigallocatechin-3-gallate (EGCG) and n-acetylcysteine. The combination addresses some or all of the pathways which can result in neurological deficiencies, degeneration and diseases.

U.S. Patent Application No. 20080213246 (Ziff and Ziff, 2008) discloses dietary supplements, compositions and methods of administering the supplements to reduce pain, inflammation and stiffness in said mammal within a few hours. The supplements and compositions can include a combination of an amino acid, vitamins, herbs and enzymes. The composition/supplement can be put in capsule form and when administered to mammals can reduce these symptoms with approximately two hours. reducing the pain and inflammation associated with chronic joint discomfort, chronic low back pain, muscle strain, arthritis, sports injuries, normal everyday bumps and bruises. The novel composition has also been shown to be very effective in reducing monthly menstrual symptoms (PMS). The novel composition can also have benefits for other ailments such as but not limited to Osteoarthritis, Cardiovascular disease, Neurological ailments, Alzheimer disease, and Cancer.

SUMMARY OF THE INVENTION

The present invention describes compositions and methods for the treatment of Post progressive supranuclear palsy, Alzheimer's disease (AD), Parkinson's disease (PD), Tauopathies or Post Traumatic Stress Disorder (PTSD), and other neurological and neurodegenerative conditions by the intravenous administration of curcumin, curcumin analogues derivatives or combinations thereof.

The present invention in one embodiment relates to a composition for ameliorating symptoms and/or treating one or more neurodegenerative diseases, neurological disorders, anxiety disorders or combinations thereof in a subject comprising: (i) one or more spherical liposomes comprising a lipid or a phospholipid wall, wherein the liposomes encloses curcumin, curcumin analogues, curcumin derivatives or combinations thereof dissolved or dispersed in an aqueous or a non-aqueous solvent with one or more optional related co-factors, proteins, antibodies, pain medications, and other pharmaceutically active agents dissolved, dispersed or suspended in the solvent, (ii) a suitable aqueous or non-aqueous dispersion medium, wherein the one or more spherical liposomes are dispersed in the dispersion medium, and (iii) one or more optional excipients, diluents, extended or controlled release agents, lubricants, preservatives or any combinations thereof. In one aspect the one or more neurological or neurodegenerative conditions disclosed hereinabove are selected from the group consisting of progressive supranuclear palsy, Alzheimer's disease (AD), Parkinson's disease (PD), Tauopathies, senile dementia, vascular dementias, Pick's disease, Creutzfeldt-Jacobs disease, and aging. In another aspect the one or more anxiety disorders comprise stress disorders, Post Traumatic Stress Disorder (PTSD), phobias, psychological traumas or combinations thereof.

In another aspect the lipid or the phospholipid is selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In yet another aspect the composition is administered intravenously, sub-cutaneously, intra-muscularly or intra-peritoneally. In another aspect the one or more liposomes have a size of about 100 nm. In a specific aspect the composition is administered intravenously.

Another embodiment of the present invention discloses a composition for ameliorating symptoms and/or treating one or more neurodegenerative diseases, neurological disorders, anxiety disorders or combinations thereof in a subject comprising: a biodegradable polymer conjugate dissolved or dispersed in a suitable aqueous or non-aqueous solvent, wherein the conjugate comprises curcumin, curcumin analogues, curcumin derivatives or combinations thereof conjugated to one or more polymers selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), copolymers, terpolymers, and combinations or mixtures thereof and one or more optional excipients, diluents, extended or controlled release agents, lubricants, preservatives or any combinations thereof. In one aspect the one or more neurological or neurodegenerative conditions are selected from the group consisting of progressive supranuclear palsy, Alzheimer's disease (AD), Parkinson's disease (PD), Tauopathies, senile dementia, vascular dementias, Pick's disease, Creutzfeldt-Jacobs disease, and aging. In another aspect the one or more anxiety disorders comprise stress disorders, Post Traumatic Stress Disorder (PTSD), phobias, psychological traumas or combinations thereof. In a related aspect the composition is administered intravenously and is a poly-lactic-glycolic-acid (PLGA)-curcumin conjugate.

In yet another embodiment the present invention provides a method for ameliorating symptoms and/or treating one or more neurodegenerative diseases, neurological disorders, anxiety disorders or combinations thereof in a subject comprising the steps of: identifying the subject in need of ameliorating symptoms and/or treatment against one or more neurodegenerative diseases, neurological disorders, anxiety disorders or combinations thereof and administering intravenously one or more pharmaceutical compositions comprising a therapeutically effective amount curcumin, curcumin analogues, curcumin derivatives or combinations thereof dissolved or dispersed in a suitable aqueous or non-aqueous medium, wherein the curcumin is enclosed in one or more spherical liposomes or is conjugated to one or more biodegradable polymers. The method as described herein further comprising the step of monitoring the efficacy of the amelioration of the symptoms or the treatment of the neurodegenerative diseases, neurological disorders or both by observing improvements in memory, cognition, learning, speech, one or more motor skills or combinations thereof in the subject and the step of monitoring the efficacy of the amelioration of the symptoms or the treatment of the anxiety disorders by observing a change in a mood or a behavior of the subject. In a related aspect of the method the liposomes comprise a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In another aspect the biodegradable polymer is selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), copolymers, terpolymers, and combinations or mixtures thereof.

In one aspect the pharmaceutical composition is a poly-lactic-glycolic-acid (PLGA)-curcumin conjugate. In another aspect the one or more liposomes have a size of about 100 nm. In yet another aspect the therapeutically effective amount comprises 50 nM/kg of body weight of the subject. In another aspect the pharmaceutical composition is optionally administered along with related co-factors, proteins, antibodies, pain medications, and other pharmaceutically active agents. In another aspect the pharmaceutically active agents comprise serotonin reuptake inhibitors, sertraline, and paroxetine.

In one embodiment the instant invention relates to a composition for ameliorating symptoms and/or treating progressive supranuclear palsy, Alzheimer's disease (AD), Parkinson's disease (PD), Tauopathies or Post Traumatic Stress Disorder (PTSD) in a subject comprising: one or more spherical liposomes comprising a lipid or a phospholipid wall, wherein the liposome encloses curcumin, curcumin analogues, curcumin derivatives or combinations thereof dissolved or dispersed in an aqueous or a non-aqueous solvent with one or more optional related co-factors, proteins, antibodies, pain medications, and other pharmaceutically active agents dissolved, dispersed, or suspended in the solvent, a suitable aqueous or non-aqueous dispersion medium, wherein the one or more spherical liposomes are dispersed in the dispersion medium, and one or more optional excipients, diluents, extended or controlled release agents, lubricants, preservatives or any combinations thereof. In one aspect the lipid or the phospholipid is selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate.

In another aspect the one or more liposomes have a size of about 100 nm. In yet another aspect the composition is administered intravenously.

In another embodiment the instant invention provides an intravenous composition for ameliorating symptoms and/or treating progressive supranuclear palsy, Alzheimer's disease (AD), Parkinson's disease (PD), Tauopathies or Post Traumatic Stress Disorder (PTSD) in a subject comprising: a curcumin, curcumin analogue, curcumin derivative, and combinations or modifications thereof conjugated with a biodegradable poly-lactic-glycolic-acid (PLGA) co-polymer, wherein the conjugate is dissolved or dispersed in a suitable aqueous or non-aqueous solvent and one or more optional excipients, diluents, extended or controlled release agents, lubricants, preservatives or any combinations thereof.

Yet another embodiment of the instant invention relates to a method of ameliorating symptoms and/or treating progressive supranuclear palsy, Alzheimer's disease (AD), Parkinson's disease (PD), Tauopathies or Post Traumatic Stress Disorder (PTSD) in a subject comprising the steps of: identifying the subject in need of amelioration and/or treatment against progressive supranuclear palsy, Alzheimer's disease (AD), Parkinson's disease (PD), Tauopathies or Post Traumatic Stress Disorder (PTSD) and administering intravenously one or more pharmaceutical compositions comprising a therapeutically effective amount curcumin, curcumin analogues, curcumin derivatives or combinations enclosed in one or more spherical liposomes or as conjugated to a biodegradable poly-lactic-glycolic-acid (PLGA) co-polymer, wherein the liposome, the conjugate or both are dissolved or dispersed in a suitable aqueous or non-aqueous medium. The method of the instant invention further comprises the step of monitoring the efficacy of the amelioration of the symptoms or the treatment by improvements in memory, cognition, learning, speech, one or more motor skills, mood, behavior or combinations thereof in the subject. In one aspect the liposomes comprise a lipid or a phospholipid wall. In another aspect the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In another aspect the one or more liposomes have a size of about 100 nm. In yet another aspect therapeutically effective amount comprises 50 nM/kg of body weight of the subject. In one aspect the pharmaceutical composition is optionally administered along with related co-factors, proteins, antibodies, pain medications, and other pharmaceutically active agents. In another aspect the one or more pharmaceutically active agents are selected from the group consisting of serotonin reuptake inhibitors sertraline, paroxetine, L-dopa, Carbidopa, benserazide, Tolcapone, dopamine agonists bromocriptine, pergolide, pramipexole, ropinirole, piribedil, cabergoline, apomorphine, lisuride, MAO inhibitors, selegiline, and rasagiline.

In one embodiment the instant invention discloses a composition for ameliorating symptoms or treating Post Traumatic Stress Disorder (PTSD) in a subject comprising: an active agent comprising curcumin, curcumin analogues, curcumin derivatives or combinations thereof dissolved or dispersed in an aqueous or a non-aqueous solvent, wherein the active agent is enclosed in one or more spherical liposomes comprising a lipid or a phospholipid wall or is conjugated with one more biodegradable polymers, one or more optional related co-factors, proteins, antibodies, pain medications, and other pharmaceutically active agents dissolved, dispersed, or suspended in the solvent, and one or more optional excipients, diluents, extended or controlled release agents, lubricants, preservatives or any combinations thereof.

In one aspect of the composition disclosed hereinabove the one or more spherical liposome or the polymer conjugate may be dispersed in a dispersion medium, wherein the dispersion medium is an aqueous or non-aqueous dispersion medium. In related aspects the lipid or the phospholipid is selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate and the one or more biodegradable polymers are selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly (amino acids), copolymers, terpolymers, and combinations or mixtures thereof.

In another aspect the composition is administered intravenously, sub-cutaneously, intra-muscularly, or intra-peritoneally. In a specific aspect the one or more liposomes have a size of about 100 nm. In yet another aspect the composition is administered intravenously.

The present invention in another embodiment provides a method of ameliorating symptoms or treating Post Traumatic Stress Disorder (PTSD) in a subject comprising the steps of: (i) identifying the subject in need of amelioration of symptoms or treatment of the PTSD and (ii) administering intravenously a therapeutically effective amount of a pharmaceutical composition curcumin, curcumin analogues, curcumin derivatives or combinations thereof dissolved or dispersed in a suitable aqueous or non-aqueous medium, wherein the curcumin is enclosed in one or more spherical liposomes or is conjugated to one or more biodegradable polymers.

In one aspect the method disclosed hereinabove further comprises the step of monitoring the efficacy of the amelioration of the symptoms or the treatment of PTSD by observing a change in a mood or a behavior of the subject. In another aspect the liposomes comprise a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In yet another aspect the biodegradable polymer is selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), copolymers, terpolymers, and combinations or mixtures thereof.

In specific aspects of the method described hereinabove the one or more liposomes have a size of about 100 nm and the therapeutically effective amount comprises 50 nM/kg of body weight of the subject. In a related aspect the pharmaceutical composition is optionally administered along with related co-factors, proteins, antibodies, pain medications, and other pharmaceutically active agents, wherein the pharmaceutically active agents comprise serotonin reuptake inhibitors sertraline and paroxetine.

In yet another embodiment the present invention relates to a composition for ameliorating symptoms or treating Parkinson's Disease (PD) in a subject comprising: (i) one or more spherical liposomes comprising a lipid or a phospholipid wall, wherein the liposome encloses curcumin, curcumin analogues, curcumin derivatives or combinations thereof dissolved or dispersed in an aqueous or a non-aqueous solvent with one or more optional related co-factors, proteins, antibodies, pain medications, and other pharmaceutically active agents dissolved, dispersed, or suspended in the solvent, (ii) a suitable aqueous or non-aqueous dispersion medium, wherein the one or more spherical liposomes are dispersed in the dispersion medium, and (iii) one or more optional excipients, diluents, extended or controlled release agents, lubricants, preservatives or any combinations thereof. In one aspect the one or more liposomes have a size of about 100 nm. In another aspect the composition is administered intravenously.

A method of ameliorating symptoms or treating Parkinson's disease (PD) in a subject is disclosed in one embodiment of the present invention. The method as disclosed herein comprises the steps of: (i) identifying the subject in need of amelioration of symptoms or treatment of the PD and (ii) administering intravenously a therapeutically effective amount of a pharmaceutical composition comprising curcumin, curcumin analogues, curcumin derivatives or combinations thereof dissolved or dispersed in a suitable aqueous or non-aqueous medium, wherein the curcumin is enclosed in one or more spherical liposomes or is conjugated to one or more biodegradable polymers. In one aspect the method further comprises the step of monitoring the efficacy of the amelioration of the symptoms or the treatment of PD by observing a change in a speech, one or more motor skills, and other functions.

In another aspect the liposomes comprise a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In a specific aspect the one or more liposomes have a size of about 100 nm. In another aspect the therapeutically effective amount comprises 50 nM/kg of body weight of the subject. In yet another aspect the pharmaceutical composition is optionally administered along with related co-factors, proteins, antibodies, pain medications, and other pharmaceutically active agents. In another aspect of the method disclosed hereinabove the one or more pharmaceutically active agents are selected from the group consisting of L-dopa, Carbidopa, benserazide, Tolcapone, dopamine agonists bromocriptine, pergolide, pramipexole, ropinirole, piribedil, cabergoline, apomorphine, lisuride, MAO inhibitors, selegiline, and rasagiline.

BRIEF DESCRIPTION OF THE DRAWINGS

For a more complete understanding of the features and advantages of the present invention, reference is now made to the detailed description of the invention along with the accompanying FIGURES and in which:

FIG. 1 is a curcumin (CCM) standard curve.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "neurodegenerative disorders or diseases" refers to diseases whose symptoms are caused by degeneration of nerve cells in the brain. A neurodegenerative disease is any disease that causes the loss of neurons in the brain, and specifically includes Parkinsonism, Huntington's disease, Alzheimer's disease, and the tremor and spasticity resulting from stroke or cerebral ischemia.

As used herein the term "neurological disorder" denotes any disorder which is present in the brain, spinal column, and related tissues, such as the meninges, which are responsive to an appropriate therapeutic agent. "Neurodegenerative disorder" refers to any disorder caused by a progressive death and disappearance of a population of nerve cells occurring in a manner characteristic of a particular disease state and leading to brain damage.

As used herein, the terms "tauopathy" and "tauopathies" refer to dementias and movement disorders that share the pathological feature of intracellular accumulations of tau. Examples of tauopathies include, but are not limited to, Down's syndrome, corticobasal degeneration, frontotemporal dementia, Pick's disease, and progressive supranuclear palsy.

The term "stress disorder" refers to a psychiatric condition precipitated by exposure to a traumatic or stressful event. Stress disorders include Acute Stress Disorder, Post-Traumatic Stress Disorder, and Brief Psychotic Disorder with Marked Stressor(s). The term "Post-Traumatic Stress Disorder" as used herein refers to a psychiatric condition in its broadest sense, as defined in DSM-IV-TR (American Psychiatric Association: Diagnostic and Statistical Manual of Mental Disorders, Fourth Edition, Text Revision, Washington, D.C., 2000). The DSM-IV-TR defines "Post-Traumatic Stress Disorder (PTSD)" as characterized by persistent re-experiencing of an extreme traumatic event. The DSM-IV-TR sets forth a generally accepted standard for diagnosing and categorizing Post-Traumatic Stress Disorder.

As used herein the term "Alzheimer's Disease (AD)" refers to a progressive mental deterioration manifested by memory loss, confusion and disorientation beginning in late middle life and typically resulting in death in five to ten years. Pathologically, AD can be characterized by thickening, conglutination, and distortion of the intracellular neurofibrils, neurofibrillary tangles and senile plaques composed of granular or filamentous argentophilic masses with an amyloid core. Methods for diagnosing AD are known in the art. For example, the National Institute of Neurological and Communicative Disorders and Stroke-Alzheimer's Disease—and the Alzheimer's Disease and Related Disorders Association (NINCDS-ADRDA) criteria can be used to diagnose Alzheimer's Disease (McKhann et al., 1984, Neurology 34:939-944). The patient's cognitive function can be assessed by the Alzheimer's Disease Assessment Scale-cognitive subscale (ADAS-cog; Rosen et al., 1984, Am. J. Psychiatry 141:1356-1364).

The term "Parkinson's disease" (PD) refers to a neurodegenerative disease especially affecting the dopaminergic neurons of the substantia nigra—pars compacta—and its nigrostriatal projections. As used herein the terms "Parkinson's disease", "Parkinson's" and "Parkinsonism" are to be understood to include the various forms of the condition including idiosyncratic Parkinson's disease, post-encephaletic Parkinson's disease, drug induced Parkinson's disease, such as neuroleptic induced Parkinsonism, and post-ischemic Parkinsonism.

As used herein the term "Curcumin (diferuloyl methane; 1,7-bis(4-hydroxy-3-methoxyphenyl)-1,6-heptadiene-3,5-dione)" is a naturally occurring compound which is the main coloring principle found in the rhizomes of the plant *Curcuma longa* (U.S. Pat. No. 5,679,864 (Krackov et al.)).

The term "liposome" refers to a capsule wherein the wall or membrane thereof is formed of lipids, especially phospholipid, with the optional addition therewith of a sterol, especially cholesterol.

As used herein, the term "in vivo" refers to being inside the body. The term "in vitro" used as used in the present application is to be understood as indicating an operation carried out in a non-living system.

The term "gene" is used to refer to a functional protein, polypeptide or peptide-encoding unit. As will be understood by those in the art, this functional term includes genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated As used herein a "biomarker" is virtually any biological compound, such as a protein and a fragment thereof, a peptide, a polypeptide, a proteoglycan, a glycoprotein, a lipoprotein, a carbohydrate, a lipid, a nucleic acid, an organic on inorganic chemical, a natural polymer, and a small molecule, that is present in the biological sample and that may be isolated from, or measured in, the biological sample. Furthermore, a biomarker can be the entire intact molecule, or it can be a portion thereof that may be partially functional or recognized, for example, by an antibody or other specific binding protein. A biomarker is considered to be informative if a measurable aspect of the biomarker is associated with a given state of the patient, for example a particular stage of sepsis. Such a measurable aspect may include, for example, the presence, absence, or concentration of the biomarker in the biological sample from the individual and/or its presence as part of a profile of biomarkers.

As used herein, the term "receptor" includes, for example, molecules that reside on the surface of cells and mediate activation of the cells by activating ligands, but also is used generically to mean any molecule that binds specifically to a counterpart. One member of a specific binding pair would arbitrarily be called a "receptor" and the other a "ligand". No particular physiological function need be associated with this specific binding. Thus, for example, a "receptor" might include antibodies, immunologically reactive portions of antibodies, molecules that are designed to complement other molecules, and so forth. Indeed, in the context of the present invention, the distinction between "receptor" and "ligand" is entirely irrelevant; the invention concerns pairs of molecules which specifically bind each other with greater affinity than either binds other molecules. However, for ease of explanation, the invention method will be discussed in terms of target receptor (again, simply a molecule for which a counterpart is sought that will react or bind with it) and "ligand" simply represents that counterpart.

As used herein, the term "treatment" refers to the treatment of the conditions mentioned herein, particularly in a patient who demonstrates symptoms of the disease or disorder.

As used herein, the term "treatment" or "treating" refers to any administration of a compound of the present invention and includes (i) inhibiting the disease in an animal that is experiencing or displaying the pathology or symptomatology of the diseased (i.e., arresting further development of the pathology and/or symptomatology) or (ii) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The terms "effective amount" or "therapeutically effective amount" described herein means the amount of the subject compound that will elicit the biological or medical response of a tissue, system, animal or human that is being sought by the researcher, veterinarian, medical doctor or other clinician.

The terms "administration of" or "administering a" compound as used herein should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

As used herein the term "intravenous administration" includes injection and other modes of intravenous administration.

The term "pharmaceutically acceptable" as used herein to describe a carrier, diluent or excipient must be compatible with the other ingredients of the formulation and not deleterious to the recipient thereof.

The present invention describes compositions and methods for ameliorating symptoms and/or treating progressive supranuclear palsy, Alzheimer's disease (AD), Parkinson's disease (PD), Tauopathies, and stress disorders including post traumatic stress disorder (PTSD). The present invention further describes the pharmacology of curcumin in humans, to identify the hippocampus as the intra-cerebral target of curcumin in the PTSD clinical setting, and to demonstrate that parenteral curcumin in appropriate dosages offers clinical benefit in a subset of patients with PTSD refractory to standard of care.

Progressive Alzheimer's dementia (AD) and Parkinson's disease (PD) constitute major cognitive and motor disease burdens among persons over 65 years of age. Pharmacologic therapy addressing clinical symptoms of cognitive and motor impairment are partially efficacious, however do not address prevention, or substantially impact upon disease progression. Cerebral environmental factors including physical trauma, psychosocial stress, chemical toxins, metabolic induced cellular injury and known genetic variants coupled with neuroinflammation, oxidative stress and protein folding distortions play precipitating or additional roles in the neurodegenerative processes of AD and PD[1]. These events also induce microglial-activated inflammatory processes which not only compromise their neuroprotective functions, but lead to release of inhibitory chemical mediators and neurotoxic cytokines[2].

The histologic presence of amyloid-beta (Abeta-1-42), in neurons and tau hyperphosphorylation are well described neuropathic changes. However, whether these are initial triggering events or secondary to other inciting neuropathologic causes is unclear. Other factors include less well defined increased cellular susceptibilities in specific brain sites: the substantia nigra pars compacta, striatum, neuronal stem and progenitor cells of the dentate gyms, and neurons of the hippocampus. Their loss or dysfunction can lead to motor and cognitive impairment syndromes. Prevention, arrest of disease progression or remediation of these disorders requires addressing a variety of molecular targets. These targets include factors triggering the neuropathic processes, microglial inflammation[2], promoting neuropathic progression, and replacing damaged or lost neurons via neurogenesis and neuroplasticity stimulation[3]. To date, remediation or neuronal replacement with extra-cerebral stem or progenitor cells remains at a pre-clinical experimental level and therapeutic benefits have been limited to symptomatic improvement.

The Hippocampus is a funnel for heavily processed sensory information that has converged at the entorhinal cortex. The hippocampus is an important critical brain complex subserving executive function, memory recall, consolidation, mood and behavioral regulation. It also has multiple functional interconnections with other sites in the brain controlling motor activity.

Perturbation of hippocampus function is the immediate cause of neuropathic disorders characterized by cognitive impairments, memory, and aberrant recall phenomena. Pharmaceutical remediation a clinical approach requires inducing neurogenesis and neuroplasticity to form recall memory, navigation, learning and to replace malfunctioning neuronal circuits[4]. Hippocampal lesions alter integration of incoming sensory or motor information with previous emotional experiences or social values. The right hippocampus and surrounding areas are activated by tasks that require explicit learning of non-verbal stimuli, and anterior hippocampal activations occur when the tasks involve remembering the relations between the stimuli. The hippocampus is involved automatically when stimuli are attended to and the amount of activation depends upon the depth of the encoding. The probabilistic classification task (Knowlton et al 1996) activates the dorso-lateral Pre Frontal Cortex and the right caudate nucleus and performance is impaired in Parkinson's Disease (PD) but not in patients with medial temporal lobe lesions. PD patients are impaired at implicit sequence learning, which is known to activate the striatum in normal subjects. During a Tower of London (TOL) task, PD patients fail to activate the right caudate nucleus, but show a task-related. Cerebral blood flow increases in the right hippocampus. This represents recruitment of the hippocampus to overcome the striatal defect. Conversely if hippocampal suppression is necessary for optimum performance, the absence of hippocampal deactivation could contribute to impaired performance on the TOL task by PD patients.

Lesions of the hippocampus are also implicated in post traumatic adjustment disorder (PTSD) which is a chronic and debilitating psychiatric disorder following life threatening events, natural disasters, accidents and trauma, returning veterans from combat, terrorist incidents, and violent personal assaults. PTSD therapy is complicated by associated disorders such as substance abuse, depression, memory and cognition problems. Lifetime prevalence rates range from 3-8% in community samples, 10-30% in disaster samples, 15-27% in war/combat veteran samples, and 20-40% in sexual assault samples. Understanding the etiology of PTSD requires mapping the cerebral neural circuitry involved in response to danger, fear conditioning and extinction learning (challenge of the conditioned fear response) are important but far more complex than a simpler pragmatic pharmacotherapeutic approach which is central to the present invention.

The estimated lifetime prevalence of PTSD, a disorder that persists for years among adult Americans is 6.8%[20]. PTSD prevalence among American Vietnam theater veterans is 30.9% for men and 26.9% for women. About 1,700,000 veterans have experienced "clinically serious stress reaction symptoms"[21]. Currently, the conflicts in Iraq and Afghanistan have a major impact on men and women serving there in terms of mental health problems. Twenty percent of 230,000 soldiers in the Iraq and the Afghanistan wars i.e., 49,425 veterans have been newly diagnosed with PTSD. The two year cost of PTSD among 1.5 million returning troops from Iraq and Afghanistan in need of evidence-based treatment is $4.3 to 6.2 billion. The two year cost per case basis ranges from $5,900 to $10,300. Contemporary therapy requires 10-12 weekly sessions, and less than 10% complete therapy. Even when the time frame of available treatment was expanded to 52 weeks less than 30% completed therapy. Only a minority of veterans who are receiving care at Department of Veterans Affairs facilities receive a recommended number of mental health treatment sessions. In addition to personal barriers there are substantial obstacles to care at the system-level. Veterans less likely to receive adequate care are male compared to female, age under 25, those diagnosed in primary care clinics and those living in rural areas. Additionally, the current treatment paradigm has shortcomings and is itself a barrier. Unmet needs of veterans with PTSD and comorbid conditions including suicide, substance abuse depression along with an array of complex medical problems emphasize the increasing demands for delivery of services in the VA system.

Within recent decades clinical disorders stemming from excessive physical and psychological trauma or undue stress has become universally recognized. The word stress refers to traumatic environmental, physical and psychological forces applied to an individual. This use of the word stress is readily understood within the context of a medical disorder. However, the variety of physical and emotional traumatic experiences inducing stress amalgamated with individual personalities render the relation between stress and a disorder ambiguous. To enhance uniformity in diagnosing and treating patients with stress-related disorders it is necessary to choose similar precipitating causes such as combat experience where the age range, intensities of exposure to death, the threat of death and physical violence encountered are relatively similar.

In 20% of veterans surviving traumatic stress, life may be marked by signs and symptoms of a debilitating stress induced mental disorder. This post-traumatic stress disorder (PTSD) is characterized by physical and emotional perturbations associated with memory processing. The propensity to develop PTSD is difficult to define since abilities to tolerate stress vary among combatants. Hence, depending upon the individual's background, exposure to similar traumatic events may be either mitigated or exaggerated and lead to PTSD. Clinical understanding and resolution of traumatic disordered memory processing, i.e., registering, storing and releasing recent and old memories center on changes in brain regions controlling memory such as the hippocampus. Anatomic perturbation, or loss of hippocampus volume technically can be imaged and correlated with PTSD. Changes in cerebral blood content and hippocampal tissue components in in vitro and animal models of stress related disorders, have unveiled some of the putative mechanisms translating stress into PTSD. These support a working hypothesis allowing screening and assessment of novel medical management options. These observations strongly suggest the hippocampus to be is a validated target associated with PTSD. Approved psychiatric drugs, cognitive psychotherapy, and social support efforts applied to treating PTSD have shown moderate but incomplete benefit since continued physiopathologic changes in conjunction with diminished neuroregenerative capacity contribute to the maintenance of the PTSD state. The increasing numbers of combat veterans with PTSD and a less than adequate medical care structure justify investments in additional therapeutic research.

Treatments include cognitive psychotherapy, however physicians preferred treatment of symptomatic PTSD patients is pharmacological, however there is a need for medications that are efficacious, have good safety profiles, are accessible, practical and affordable so that patients in diverse contexts can profit from them. Currently approved treatments include serotonin reuptake inhibitors sertraline and paroxetine, for treating PTSD in adults, however improvement is not universal with these treatments, and use in clinical practice and community-based health care settings is spotty.

Curcumin has been reported to address these issues, by stimulating hippocampal progenitor and stem cells in vitro and to reverse impaired hippocampal neurogenesis[3]. In an in vivo study curcumin prevented stress-induced decreases of 5-HT(1A) mRNA, brain derived neurotrophic factor (BDNF) protein levels and stimulated neurogenesis through the serotonin-1-A receptor and BNDF[5]. Hypothetically with induced neuroplasticity and migration these new neurons may replace damaged or destroyed neurons at other sites in the brain. In order to prevent, arrest, or repair progressive neuronal deterioration, pharmaceuticals must be able to passage across the blood brain barrier and the brain parenchyma with little or no accompanying adverse events, must be managed by appropriate drug transporters within the parenchyma and must accumulate in therapeutic concentrations in affected sites.

Curcumin as used in the present invention offers several unique features making it an attractive candidate for the treatment of PTSD and PD. (i) curcumin prevents death of neurons in animal models of neurodegenerative diseases, (ii) curcumin exerts biphasic effects (low conc.=mutagenesis, high conc.=inhibit) on murine multipotent neural progenitor cells (NPC) in the developing and adult dentate gyms of the mouse hippocampus, (iii) curcumin activates extracellular signal-related kinases (Arks) & p38 kinases: increases neuronal plasticity, enhances neurogenesis and with Nrf2-ARE in tumor cells induces home oxygenize which in neurons is a cytoprotective protein, (iv) curcumin inhibits growth-factor signaling pathways coupled to ERKs and protein kinase C in tumor cells, (v) curcumin reduces oxidative damage and cognitive deficits associated with aging, (vi) curcumin protects hippocampal neurons against excitotoxic and traumatic injury, (vii) curcumin directs free radical scavenging properties in high μMol concentrations, low concentrations can activate/inhibit signal transduction pathways, (viii) At 0.1-0.5 μM (500 nM)×24-48 h increases NPC proliferation but not tumor cells; >10 uM decreases proliferation of NPCs, and cancer cells, and (ix) systemic i.p. curcumin @ 500 nM/kg×4 days→peak concentration of 5-6 μM in the blood and 1-2 μM in the brain.

The present invention discloses a major improvement in PTSD clinical management. The inventors plan to administer intravenous liposomal curcumin in veterans diagnosed with post-combat PTSD and will assess its safety and efficacy. This drug crosses the blood brain barrier, localizes in the hippocampus and striata, prevents stress-induced neuronal cell damage, and stimulates neurogenesis and remediation of damaged neural circuits.

The change in the therapeutic paradigm of PTSD using a chemotherapeutic agent specifically targeted to stress-induced damage of critical neuronal sites as described hereinabove may prove to be a more effective treatment of an unresolved problem.

The issues of increasing numbers of combat veterans with PTSD, a stochastic time course of occurrence of clinical signs and symptoms, chronicity requiring acute and long-term interventions, premature status of objective diagnostic methods, inadequacy of standard of care and delivery, and excessive cost of psychological approaches and current treatment methods justify a novel treatment paradigm of the instant invention. The needs justifying the new treatment paradigm described herein are the consequences of the increasing population of post-combat veterans with significant emotional and co-morbid problems, cost of medical management, societal disruptions, instability and decreased productivity in the civilian work force. Although premature to consider, the addition of effective therapy may allow a remote possibility of a preventative component serving to diminish traumatic stress related disorders and improve the overall functioning in the battlefield of armed forces personnel.

The present invention resolves an unmet medical need, diminishes cost of medical and social repercussions and the potential for extrapolation to the civilian experience of stress related disorders. In this affected population there are co-morbid conditions such as alcohol abuse, smoking, drug addiction, and suicide which if ameliorated would be of significant benefit. Because there is a need for treatment of disorders associated with hippocampus defects in aging, and other neurodegenerative dementias, diagnosing and treating hippocampus lesions following traumatic stress presents several pragmatic advantages.

Validation of the problem can be gauged from existing reports of the number of PTSD affected individuals[20], the estimated and increasing costs of psychological and medical interventions, and the loss to society of inadequately treated individuals with chronic PTSD. Positive financial and productivity repercussions in the population will follow objective and symptomatic improvement in PTSD individuals.

EXAMPLE I

Use of Curcumin in Neurodegenerative and Neurological Disorders

Hippocampal neurogenesis is increased in response to environmental conditions, which improve learning & memory, such as exercise, and dietary energy restriction and compromised by A.D., aging, diabetes. Hippocampal neurogenesis is enhanced by curcumin; at 500 nM. Curcumin improves chronic unpredictable mild stress (CUMS) by inducing low sucrose consumption, lowering serum corticosterone, enhancing adenylyl cyclase (AC) catalytic activity, and cAMP levels in various brain regions, up-regulated mRNA expressions of AC subtypes AC2, AC8, and cAMP response element binding protein (CREB) in the hippocampus, cortex, and hypothalamus of CUMS rats. Rationale for it being an anti-depressant[17]. Curcumin improves the memory ability of Alzheimer's Disease mice (ALCL3 orally and D-galactose IP for 90 days) using the step-through test and prolonged step through latence and inhibits apoptosis induced by AlCl3 in cultured PC12 cells. Mechanism indicated increased BCL-2 but not Bax[18]. Curcumin has antioxidative, antilipofusinogenesic, and anti-aging effects in aging rats[19].

The present inventors have developed curcumin for neuropathic applications based upon in vitro data with curcumin in brain-derived adult neural stem cells where it stimulated neurogenesis, synaptogenesis, and migration[3]. Additional animal and biochemical analyses revealed that curcumin also acts as an antioxidant[6], has epigenetic effects: it decreased histone H3 and H4 acetylation i.e., it behaved as a histone acetyltransferase inhibitor as well as a histone deacetylase inhibitor[7,8]. These activities tend to suppress differentiation in astrocytes while promoting neuronal differentiation.

Due to curcumin insolubility in aqueous media and minimal bioavailability when administered by the oral route the present inventors developed liposomal curcumin, polymeric nanocurcumin (Nanocurc®), and poly-lactic-glycolic-acid co-polymeric (PLGA) curcumin, blood soluble formulations for intravenous administration[9,10,11]. The curcumin in these formulations was synthesized to 99.2% purity under GMP conditions. The inventors determined passage of these three formulations across the blood brain barrier and intracerebral tissue pharmacokinetics in rats following the intravenous bolus injection to determine curcumin distribution within the parenchyma and possible localization in specific brain regions associated with neurological disorders.

Curcumin was synthesized to 99.2% purity by Sami Labs, Sabinsa Corporation, Bangalore, India and used in the liposomal, PLGA curcumin and Nanocurc® formulations. PLGA was bought from Surmodic Pharmaceuticals, Inc. Birmingham, Ala., and the PLGA-curcumin formulation was synthesized in the University of North Texas Health Sciences Center, Ft. Worth, Tex. Nanocurc® was synthesized at Johns Hopkins Hospital Cancer Center using acrylic polymers bought from Surmodics Inc. Liposomal curcumin was synthesized at Polymun Scientific GmbH, Vienna Austria.

Sprague-Dawley rats weighing 250 grams were purchased from Charles River PQ Canada and allowed to acclimatize to a 12 hour light-darkness cycle over seven days. They were given access to a commercial chow, tap water and maintained strictly within the guidelines of institutional animal care. The investigational protocol was approved by the University of Western Ontario, Canada Animal Health Care Committee. The caudal vein was chosen as a route for drug administration because it required minimal restraint and induced little stress. Liposomal curcumin was injected as a 20 mg/kg bolus without dilution. Nanocurc® was solubilized in 0.9% normal saline and administered as a 5 mg/kg bolus, and PLGA curcumin dissolved in double distilled water was administered as a 20 mg/kg bolus. At time intervals following injection, blood samples were collected by cardiac puncture, following which the rats were euthanized by ketamine anesthesia. For each dose and time intervals of one, two and four hours after intravenous injection. three to four rats were used. Following ketamine euthanasia, their brains were immediately removed, and portions of the cortex, left and right hippocampus, brain stem (medulla, pons, and midbrain), and striatum were dissected on an ice bed weighed and prepared for HPLC analysis. Other brain regions, plasma, spleen, kidneys, and liver were weighed, quickly frozen in liquid nitrogen and stored for further analyses.

The weighed specimens were homogenized in 20% PBS. Two hundred microliters of each homogenized brain tissue was transferred to amber, labeled microcentrifuge tubes to which 200 µL of an internal standard of acetonitrile solution 0.15 µL/ml (IS) was added. For curcumin standards, 180 µL of homogenized curcumin-untreated brain tissue was transferred to four amber, labeled microcentrifuge tubes. Then 20 µL of known curcumin standards (0.5 µg/mL, 1.25 µg/mL, 2.5 µg/mL, and 5.0 µg/mL), respectively were added with 200 µL of 0.15 µL IS solution. For the blank negative control, 200 µL of homogenized control brain tissue and 200 µL IS solution was added All samples, controls, and standards with IS were vortexed for 10 minutes, and then centrifuged for 5 minutes at 6000 RPM. After removing and filtering the supernatant of each sample through 0.22 µM nylon syringe filters, 50 µL of each sample was injected into the HPLC system. For plasma determinations, 200 µL of each plasma from each rat was transferred into amber, labeled microcentrifuge tubes to which 200 µL of IS was added. For curcumin standards, 180 µL curcumin-untreated plasma was added to into four microcentrifuge tubes and 20 µL of curcumin (0.5, 1.25, 2.5 and 5.0 µg/mL, respectively) added with 200 µL of IS solution. For the blank negative controls, 200 µL control plasma and IS solution were used. All samples, controls and standards with internal standards (IS) were vortexed for 10 minutes and then centrifuged for five minutes at 6000 RPM. The supernatants of each sample were passed through 0.22 µM nylon syringe filters, and injected in a final volume of 50 µL into the HPLC system.

Curcumin standard and Emodin as the internal standard were purchased from the National Institute for the control of Pharmaceutical and Biological Products (Bejing, China). This curcumin standard was compared with GMP grade curcumin synthesized by Sabinsa Inc., Bangalore, India. For curcumin determinations in plasma and tissues, the inventors used the method adopted by Li[13].

The method of the present invention closely follows US good laboratory practices (GLP) guidelines. The HPLC analysis was carried out on a Water HPLC System consisting of Waters 1525 binary pumps, 2487 Dual absorbance detector and Waters Breeze Software, 3.3 version (Waters, Mass., USA). The curcumin measurements were determined using the Waters HPLC system with an Inspire C18 column (4.6× 100 mm, 5 µm particle size,) Kikma Technologies, Bejing, China.) The mobile phase was composed of acetonitrile and 5% acetic acid, (75:25, v/v) at a flow rate of 1.0 mL/min. The mobile phase was filtered through a 0.45 µM nylon membrane filter and ultrasonically degassed prior to use. The detection wavelength was 420 nm. The injection volume was 50 µL and the analysis time was five minutes per sample at room temperature.

The relative area of plasma liposome curcumin standard was linear within the range of 1 µg-12 µg/5.0 µL of the sample as determined by HPLC, as shown in the standard curve (FIG. 1). In the absence of any prior or concomitant chemical or physical manipulation, for the liposomal formulation the tissue curcumin:blood curcumin ratio in the hippocampus and the pooled-brain was greater than unity at the 4-hour time interval. Similarly, the striatum:blood: ratio at two hours for PLGA curcumin indicated that tissue measurements did not reflect vascular curcumin and that these formulated compounds pass the blood brain barrier, as shown in Tables 1-3. Localization and clearance rates of the three formulations varied suggesting that the individual formulations may have modulated the cerebral PK characteristics.

Curcumin was detectible primarily in the hippocampus, brainstem and striatum at levels less than 0.5% of the total injected dose. Liposomal curcumin concentrations in the hippocampus and striatal regions peaked at two hours. Pooled brain regions other than the striatum and the hippocampus had lesser or no detectable curcumin suggesting preferential deposition. Clearance rates relative to the injection time in these two sites also varied. At two hours the striatum had twofold greater curcumin content than the hippocampus and following peak concentrations, clearance in the striatum was greater than in the hippocampus (Table 1).

TABLE 1

Mean brain tissue and plasma curcumin levels in rats following intravenous liposomal curcumin (20 mg/kg).

|  | 2 hrs post injection | 4 hrs post injection | Tissue/Plasma ratio 2 hrs | 4 hrs |
|---|---|---|---|---|
| Striatum (ng/g) | 165 ± 72.2 | 12.0 ± 7.4 | 1.00 | 0.81 |
| Hippocampus (ng/g) | 83.0 ± 35.0 | 41.0 ± 40.0 | 0.50 | 2.61 |
| Pooled Brain (ng/g) | 43.0 ± 38.1 | 62.0 ± 61 | 0.23 | 4.01 |
| Plasma (ng/mL) | 166 ± 15.0 | 15.4 ± 13.2 |  |  |

Values are expressed as mean ± SEM. (n = 4 at each time interval)

Nanocurc® distribution studies at 5 mg/kg a dose reduction in total curcumin injected was due to a limited supply. There was notable accumulation in the brainstem, and a hippocampus localization rate slightly greater than observed with the liposomal preparation with overall slower clearance rates from the striatum (Table 2). In this study clearance from the plasma between one and two hours was less than that observed with liposomal curcumin. The decline in brain tissue curcumin levels did not proportionally follow the fall in plasma. It is logical to assume curcumin levels observed at one hour would be higher than at two hours. Following Nanocurc®, higher levels of curcumin in the hippocampus than in the striatum compared to liposomal curcumin are noted.

For PLGA-curcumin at 20 mg/kg the IV dosage of curcumin was 2 mg/kg when corrected for the ratio of PLGA to curcumin (Table 3). Uptake was highest in the striatum, followed by the hippocampus and the brainstem. A high brain tissue/plasma ratio was observed at 2 hours post-IV injection. Four hours post injection the plasma curcumin level decreased 50% while both striatal and brainstem curcumin levels were undetectable. Hippocampus curcumin levels remained relatively constant four hours post-injection.

TABLE 2

Mean brain tissue and plasma curcumin levels in rats following intravenous Nanocurc ® (5.0 mg/kg).

|  | Mean tissue and plasma curcumin levels | | Brain/Plasma ratio | |
|---|---|---|---|---|
|  | 1 hr post injection | 2 hrs post injection | 1 hr | 2 hrs |
| Striatum (ng/g) | 69.0 ± 9.05 | 48.18 | 0.018 | 0.024 |
| Hippocampus (ng/g) | 80.0 ± 11.9 | 54.41 | 0.020 | 0.027 |
| Brain Stem (ng/g) | 120 ± 22.78 | 235.08 | 0.031 | 0.12 |
| Plasma (ng/mL) | 3913 ± 924 | 1980.01 |  |  |

Values are expressed as mean + SEM for the 1-hour group (n = 2) and for the 2-hour group (n = 1). Total curcumin as the active principal ingredient injected is 1.6% or 0.08 mg/kg due to limited supply of nanocurc ® at the time of this study.

Following intravenous bolus administration of curcumin formulations, passage across the blood brain barrier of rats was demonstrated. Passage across the blood brain barrier and anti-inflammatory, and antioxidant properties in their brains was not surprising based upon previous studies with Nanocurc® given intraperitoneally in mice[6]. Crossing the blood brain barrier by formulated curcumin may occur or be promoted by trans-membrane diffusion, saturable transport, absorptive endocytosis, and extracellular pathways and MDR-1 inhibitory activity. The impact of the solubilizing components on drug diffusion, transport and clearance from the brain parenchyma is unclear as is the fate of the liposomal, polymeric and PLGA chemical structures, however they could contribute to the variances in localization and clearance differences noted among the three formulations.

TABLE 3

Mean brain tissue and plasma curcumin levels in rats following intravenous PLGA-curcumin (20 mg/kg).

|  | Mean tissue and plasma curcumin levels | | Brain/ Plasma ratio | |
|---|---|---|---|---|
|  | 2 hrs post injection | 4 hrs post injection | 2 hrs | 4 hrs |
| Striatum (ng/g) | 23.3 ± 13.4 | 0 | 2.8 | — |
| Hippocampus (ng/g) | 5.2 ± 8.2 | 5.1 ± 5.2 | 0.63 | 1.1 |
| Brain Stem (ng/g) | 5.3 ± 5.4 | 0 | 0.65 | — |
| Plasma (ng/mL) | 8.2 ± 4.5 | 4.5 ± 4.6 |  |  |

Values are expressed as mean + SEM. n = 3/group. For curcumin-PLGA, the purity of free curcumin is 99.2 % and the relative ratio of free curcumin to the PLGA copolymer is 1:9, hence the intravenous dose of free curcumin in the Curcumin-PLGA formulation is 2 mg/kg.

While the dosages were different in these studies, the importance is that curcumin formulations pass the blood brain barrier, a therapeutic obstacle to treatment of neuropathic disorders. Because of availability of drug, a limited number of rats, and sampling times for each formulation tested. Detectable differences among the three formulations in different sites reflect the net effect of blood flow, influx, residence, and efflux properties. Vascular anatomy of different sites in the rat may be considered a contributing factor, however the high striatum and brainstem levels in the liposomal and Nanocurc® injected rats respectively, may not extrapolate to humans since studies correlating local blood flow with high resolution anatomy in patients did not disclose any relative increase in vascularity in the hippocampus. striatum and brainstem compared to the rest of the brain[14]. Different accumulation rates and clearance parameters may reflect site specific variable anatomic features such as interstitial extracellular compartments, transport distance from the vasculature and interstitial pressure. High interstitial pressure with outward radial convection regions can block extravasation of drug and fluids by opposing inward diffusion and also reduce the rate of transport across the extracellular fluid compartment.

Focal distribution and uptake of these three curcumin formulations in specific brain regions, and mechanisms contributing to this selective site localization remain cryptic and cannot be explained by passive processes that depend upon physicochemical characteristics such as lipophilicity or molecular weight. There is however a possible role for intracerebral drug transporters influencing curcumin pharmacokinetics and site localization. These transporters eliminate organic anions (OAT) or cations (OCT) from the brain and are widely expressed in the hippocampus, cerebellum and cerebral cortex. Their role is to prevent accumulation of xenobiotics, neurotoxins, and neurotransmitters. Since PLGA molecules are negatively charged, utilization of the OAT conduit may contribute towards localization however this does not explain the lack of distribution to the cerebellum and cortex.

All of these features impact on time from extravasation till the drug reaches the periphery of the cellular site of interest and are independent of diffusion rates which depend upon the size of the molecule. The larger the molecule size, the lower the mobility and intrinsic diffusion rate.

While intracerebral curcumin distribution can be partly described by accounting for several inter-compartmental parenchymal transport parameters, and compartmental modeling of unbound brain/plasma concentrations what still remains cryptic are mechanisms and components contributing to distribution, localization, and retention time in the hippocampus, striatum, and brainstem compartments. Curcumin may not be unique in its pharmacological actions as reflected in specific cerebral localization patterns of different compounds. Indirect evidence comes from a study of oral sodium arsenite in rats; the arsenite, when administered at the dosage of 20 mg/kg for 28 days, induced neuro-behavioral neurotransmission toxicity as reflected in the severity of oxidative stress, altered dopaminergic functions, biogenic amines, metabolites, and nitric oxide in the corpus striatum, hippocampus, and the frontal cortex. These deleterious effect were counteracted by simultaneous treatment with massive oral doses of curcumin 100 mg/kg daily×28 days[15].

The specific distribution of curcumin in therapeutic concentrations is evidence for potential efficacy of curcumin treatment of neuropathic disorders. Differences in clinical responses to curcumin formulations and rates of administration (dosage) may occur based upon observations of different cerebral localization rates. A bolus dose (drug delivery of higher concentration in a brief time period) can improve lesioned sites at the expense of adverse normal surrounding tissue toxicity particularly in the absence of compensating clearance at the lesion site. For example, drug entry and clearance from the cerebral and peripheral nerve circulation is affected by the blood brain barrier, whereas intrathecal administration of small lipid soluble drugs may be ineffectual because of a large brain to blood efflux. Intravenous constant infusion of a drug at a dosage calculated to deliver reduced normal tissue toxic effects may be accompanied by increased therapeutic effects depending upon the sensitivity of the target cells. This is particularly applicable to hippocampus stem and neuronal progenitor cells where low concentrations of curcumin (500 nM) stimulate, and high concentrations (10 µM) inhibit neurogenesis and neuroplasticity[3].

The goals of treating neuropathic lesions require arresting degenerative processes and remediation. Regarding these three formulations, a formulation exhibiting slow release of the active principle may present clinical advantages relating to greater molecular stability in a lipid environment, enhanced permeability across the interstitium, cell uptake and retention in select sites. Contributing to this are its fundamental physicochemical properties, i.e. size, charge, and hydrophobicity. Efficacy in patients may also depend upon the disease stage, location type of lesion, localization and retention of active substance. In general, requirements for treating lesions with the highest correction probability depend upon their spatial profile. Neuropathic lesions associated with neurologic disorders have either a non-dispersed spatial profile (relatively discrete loci as in Parkinson's disease or PTSD), or a dispersed-non-dispersed profile depending upon maturity of disease (Alzheimer's disease) which may impact upon the ameliorative efficiency of curcumin.

Normal adult brain cells are sessile and following curcumin exposure may be functionally improved or suppressed depending upon drug concentration. Additional factors affecting curcumin efficacy include drug infusion rates, infusion durations, tissue penetration, site specificity, clearance from blood into lesion, convection constants for both lesional and normal tissues (if increased the probability of corrected lesion also increases, since in the brain diffusion alone is imprecise and convection caused by infusion predominates), and lesional growth rate or progression of disease. These same parameters hold for neuronal precursor cells in the dentate gyms of the hippocampus. These are susceptible to neurogenesis inducing agents (low concentration curcumin, epidermal growth factor, physical activity). Within this context the targetable neuropathic lesion of interest may have a high cell density or highly concentrated spatial profile rendering it more amenable to therapy. Drug clearance factors are similarly important since if reduced, and in the presence of increased drug penetration, and non-dispersed spatial drug distribution, an increased probability of correction may follow.

In studies with rats, after intravenous injection of liposomal curcumin, polymeric nanocurcumin, and PLGA-curcumin passage through the blood brain barrier and distribution to putative neuropathic disease-associated sites suggest the obstacles to therapeutic utility of curcumin in brain diseases may be overcome. Evaluating animal models with chemically or radiologically diseased hippocampus, or striata should allow determination as to which of the three formulations is optimum therapeutically.

Since curcumin can act on hippocampal stem cells as a mitogen and induce integration of these cells into a functional neurological system it should induce remediation for lost or damaged hippocampal neuronal stem cells[3] in AD and PD. In support of this possibility intraperitoneal curcumin was demonstrated to have neuroprotective activity against homocysteine directly injected into the hippocampus[16].

The data presented hereinabove indicate that following intravenous injections, curcumin formulations composed of liposomes, acrylic polymers (Nanocurc®), and PLGA cross the blood brain barrier and preferentially localize in the hippocampus, the striata, and brain stem. These observations of curcumin localization in specific brain sites at concentrations considered to have antioxidant, anti-inflammatory, neurogenesis and neuroplasticity activity support clinical applications of prevention, therapy, and remediation of several neuropathic disorders including Alzheimer's and Parkinson's disease. Since the formulation and dosage-dependant accumulation rates and residence times in these specific sites may govern their clinical efficacy, data concerning scheduling and dose-response characteristics of each of the formulations in animal models of neuropathic disorders are required to plan and execute an evidence-based treatment paradigm for clinical trials.

EXAMPLE II

Use of Curcumin in Post Traumatic Stress Disorder (PTSD)

Curcumin was chosen as the lead compound by the present inventors based upon its use as a medicinal in traditional therapy, and publications exploring its chemical, and pharmacologic properties in in vitro and in rodents. The present inventors used three intravenous formulations, liposomal, polymeric, and a targeted antibody-PLGA-nanocurcumin. These formulations circumvented curcumin's limited solubility and negligible oral bioavailability.

The inventors demonstrated proof of distribution of intravenous liposomal and polymeric nanocurcumin across the blood brain barrier in mice and localization in the rat brain: predominantly in the striata and the hippocampus. Two hours after intravenous injection of 20 mg/kg of liposomal curcumin in rats, the mean curcumin levels (ng/g) in the striatum were 165.3, in the hippocampus they were 83.4 in the pooled brain 42.8, and in the plasma 165.7 ng/ml, which could be explained by redistribution from the brain to the plasma. This observation of preferential liposomal curcumin in the hippocampus and the striatum is central to the therapeutic approach presented herein, because it coincides with previous studies reporting that curcumin stimulates neurogenesis in the hippocampus in vitro and in vivo[23]. The inventors demonstrated that liposomal curcumin was active against cancers of the pancreas, breast, and colon in animal xenograft models. In contrast to published data emphasizing safety with oral administration, it was observed by the inventors that hemolysis was a major adverse reaction in dogs at doses greater than therapeutic levels.

The Hippocampus is a funnel for heavily processed sensory information that has converged at the entorhinal cortex. Hippocampal lesions alter integration of incoming sensory or motor information with previous emotional experiences or social values. The right hippocampus and surrounding areas are activated by tasks that require explicit learning of nonverbal stimuli, and anterior hippocampal activations occur when the tasks involve remembering the relations between the stimuli. The hippocampus is involved automatically when stimuli are attended to and the amount of activation depends upon the depth of the encoding. The probabilistic classification task (Knowlton et al 1996) activates the dorso-lateral Pre Frontal Cortex and the right caudate nucleus and performance is impaired in Parkinson's Disease (PD) but not in patients with medial temporal lobe lesions. PD patients are impaired at implicit sequence learning, which is known to activate the striatum in normal subjects. During a Tower of London (TOL) task, PD patients fail to activate the right caudate nucleus, but show a task-related. Cerebral blood flow increases in the right hippocampus. This represents recruitment of the hippocampus to overcome the striatal defect. Conversely if hippocampal suppression is necessary for optimum performance, the absence of hippocampal deactivation could contribute to impaired performance on the TOL task by PD patients.

Neural Progenitor Cells (NPCs) are source of all neurons and glial cells in the brain during embryonic development. In adult brain hippocampus & subventricular region of cerebral cortex retain NPCs capable of migrating, dividing, & differentiating into neurons. NPCs are mitogenic and survival response to physical exercise, dietary restriction, injury. Chronic stress impairs NPC proliferation, which is reversible with curcumin. Adult neurogenesis has a role in learning and memory processes.

Curcumin as used in the present invention offers several unique features making it an attractive candidate for the treatment of PTSD and PD. (i) Curcumin prevents death of neurons in animal models of neurodegenerative diseases, (ii) Curcumin exerts biphasic effects (low conc=mitogenesis, high conc=inhibit) on murine multipotent neural progenitor cells (NPC) in the developing and adult dentate gyms of the mouse hippocampus, (iii) Curcumin activates extracellular signal-related kinases (ERKs) & p38 kinases: increases neuronal plasticity, enhances neurogenesis and with Nrf2-ARE in tumor cells induces heme oxygenase which in neurons is a cytoprotective protein, (iv) Curcumin inhibits growth-factor signaling pathways coupled to ERKs and protein kinase C in tumor cells, (v) Curcumin reduces oxidative damage and cognitive deficits associated with aging, (vi) Curcumin protects hippocampal neurons against excitotoxic & traumatic injury, (vii) Curcumin directs free radical scavenging properties in high uMol concentrations, low concentrations can activate/inhibit signal transduction pathways, (viii) At 0.1-0.5 uM (500 nM)×24-48 h increases NPC proliferation but not tumor cells; >10 uM decreases proliferation of NPCs, and cancer cells, and (ix) Systemic i.p. curcumin @ 500 nM/kg×4 days→peak concentration of 5-6 uM in the blood and 1-2 uM in the brain.

Hippocampal neurogenesis is increased in response to environmental conditions, which improve learning & memory, such as exercise, and dietary energy restriction and compromised by A.D., aging, diabetes. Hippocampal neurogenesis is enhanced by curcumin at 500 nM A Putative Solution to the PTSD Problem: Using in vitro and animal models of stress related disorders, changes in cerebral blood and hippocampal tissue components have unveiled some of the physiopathology of the hippocampus lesions. There are also human imaging studies demonstrating functional changes in key brain areas. Review of changes in brain plasticity in PTSD has shown that the sites implicated in core symptoms of PTSD: hyper-arousal, intrusive imageries, nightmares and emotional numbing, are the medial prefrontal cortex, hippocampus and the amygdala. There is evidence in support of the negative impact of stress on hippocampal neurogenesis in PTSD. Antidepressants, milieu changes and physical exercises have some beneficial effects on reversing stress-induced neurogenesis. However, specific drug candidates targeting neurogenesis are lacking.

Epigenetic mechanisms have been proposed as contributors to the pathophysiology of PTSD. However, it is a challenge to associate limited epigenetic observations with putative drug candidates. Unlike determinants of gene structure, epigenetic signaling focuses on specific gene products being "turned on or off". Some components of epigenetic mechanisms i.e., DNA-methylation and the balance between histone acetylation and deacetylation may modify the clinical course of PTSD.

Transcriptional activation following stressful events results in memories being encoded in the dentate gyms along with phosphorylation and acetylation of histone H3. Previous studies have demonstrated that curcuminoid HDAC inhibitory activity behaves as a histone deacetylase and may impact on memory mechanisms in the hippocampus.

The formulation of curcumin as nanosized liposomal curcumin as disclosed herein provides a rare opportunity to decipher the complexities of epigenetics or gene-environment interaction in PTSD and to further explore curcumin therapy within the context of its novel HDAC inhibition. Liposomal curcumin localization in the hippocampus and the implementation of clinical trials as described herein with the intravenous formulations as a possible amelioration of PTSD requires an understanding of the roles of trauma, and the hippocampus as the critical center for memory processing. The hippocampus functionally depends upon a variety of sensory inputs. Once information has arrived at the hippocampus, it processes and stores it. The information may lie indolent or be actively transferred to a variety of motor and sensory effectors and manifested clinically as emotion. The mechanism by which it incorporates, retains, recalls and elicits emotional reactions establishes the context by which any particular stressful event is managed. Hence, the health of the hippocampus is a measure of tolerance to stress. Stressors in the form of extreme physical trauma, or psychological life-threatening events or a combination of both can result in pathologic injury to the cells of the hippocampus and reduce tolerance to recurrent stress. The end result of induced damage may contribute to the pathophysiology of PTSD and comorbid depression[23].

An important query is why should this particular site be susceptible to indirect trauma. Compared to a relatively simple conditioned or evolutionarily conserved reflex there are many intricate "moving parts" characterizing its plasticity and adaptability rendering it susceptible to injury. This susceptibility appears to be compensated by the presence of neuronal stem/precursor cells representing a fail-safe mechanism to account for loss of neurons due to normal wear and tear, aging, and undo trauma induced stress. Exploration of pharmacologic interaction with these cells is very limited at present[23].

The probability of encountering serious adverse circumstances where traumatic physiopathology affecting the hippocampus is not uncommon in combat situations. When such circumstances occur the individual may exhibit immediate or delayed signs and symptoms characterizing PTSD. This diagnosis was first codified in 1980 with the publication of the DSM-III. Thus identifying individuals with PTSD requires a history of trauma, and for successful clinical management additional investigation to determine which components of the disorder which may be remediable and which may be resistant to contemporary therapy because of pathologic neuronal cell loss. Because of the long, time-consuming manpower demanding, multifaceted approach, complete re-introduction of the PTSD veteran into normal functioning society constitutes a major financial burden for the individual and for society. The contemporary range of conventional and experimental treatments include a varied psychiatric spectrum of maneuvers, a chemotherapy approach incorporating treatments with a number of drugs developed to treat other psychological disorders such as anti-depressants, anxiolytics, mood elevators etc.

The possibility that a centralized stress-associated damaged locus such as the hippocampus could be a main therapeutic target is that it is composed of several unique features. In addition to being a memory-processing center it is sensitive to direct physical and indirect psychological trauma, denervation with aging, and vasculopathies. Hippocampus dysfunctions are associated with other neuropathies such as Alzheimer's Disease, Temporal Lobe dementias, and Parkinson's disease. On the positive side, the presence of neuronal stem cells allow the possibility of autonomous or induced mitogenic stimulation and repair or reconnection of neural complexes. This latter opportunity has sparked interest in active neuroregenerative-based repair research, since damage-induced spontaneously reversible activities are excluded from examination outside of animal models. The availability of non-invasive techniques, such as PET scans for measuring function or size, are becoming valuable as improved detection of lesioned hippocampi has become a possibility.

The working hypothesis, but in no way a limitation of the present invention, is that PTSD is related to hippocampus neuropathology secondary to acute and severe stress. There are no current chemotherapeutics addressing the issues of repairing this disorder at the level of the hippocampus. This requires drug distribution to the involved site, and neuronal-repair anticipating that induction of autologous replacement of lost or damaged neurons will result in reversing the dysfunctional aspects of the hippocampus. This latter possibility can be examined using a representative animal model, Liposomal curcumin answers the requirement for a drug that pass the blood brain barrier, is not toxic to normal brain tissue at appropriate concentrations, is localized in the hippocampus following parenteral infusion, and act as a neuronal stem cell mitogen. With this background and considering the hippocampus is a critical therapeutic target, clinical trials of intravenous liposomal curcumin, a novel chemotherapeutic agent may prove beneficial for PTSD. This is because, exposure to traumatic physical or emotional events are retained as memory in the hippocampus and associated storage sites in the brain. This process can be viewed either as a component of a survival mechanism allowing adaptation to recurrent hostile events or depending upon the strength of the stimulus, perturbation of neurotrophic factors, stress hormones epinephrine and norepinephrine and lowered levels of cortisol, physiopathologic induced damage to the hippocampus. When morphologically and functionally disordered, continual stress responses, uncontrolled recall of "flight or fight" responses from stored memory may be activated intrinsically or stimulated from additional input. This may be the root cause of clinically recognizable sociopathologic conditions presenting as memory aberrations and PTSD. The mechanism of intrinsic events contributing to recall phenomena in the absence of external stimuli may be because of a lack of inhibitory signals to hyperactive hippocampal neurons. These observations point to the hippocampus as a central component in PTSD.

To validate the hippocampus as a target in PTSD it is necessary to demonstrate that when damaged it is associated with clinical signs and symptoms of PTSD and when therapeutically improved with acceptable safety liability a clinical benefit results. Evidence of target validation stems from non-invasive diagnostic imaging of the hippocampus where reduced size is demonstrated in several neuropathic conditions and where hippocampal pathology is related to symptoms (re-experiencing the traumatic event is a hallmark symptom). Here the activity of the effector, i.e. perturbed hippocampus tissue translates into a clinical syndrome of abnormal mental expression. Based upon morphologic changes; loss of neurons and neuronal stem cells following aging or and sensory/physical trauma in the hippocampus this locus is considered a prime target to address pharmacologic interventions. Limited pharmacologic and experimental data on hippocampus neurons and neuronal stem cells support a target modulation-based model of disease[4]. This does not exclude modification of other target sites such as the amygdala, or sites producing regenerative neurotrophic factors, degenerative stress hormones, or modulating the receptors for these substances which may also contribute to PTSD.

PTSD appears to be a polygenetic disorder, i.e., there are several genes that contribute additively. Genetically distinct mouse strains reared in identical environments show variation in response to fear conditioning suggesting there are genetic mutations in this model which can mimic the condition[24]. In humans, a relation between genotype and disease process is suggested by the observation that Cambodian refugee children whose parents had PTSD were five times more likely to receive the diagnosis than children whose parents did not develop PTSD[25]. In twin studies, substantial genetic influences were found in both combat experience and non-veteran community samples[26]. The most robust genetic association in study of PTSD described a positive association between a polymorphism in the dopamine transporter gene SLC6A3 3' and PTSD[27]. This latter observation may have some relevance to the localization of liposomal curcumin in the striata, a dopaminergic neuronal target[28]. The present inventors attempt to demonstrate the hippocampus as a valid target in pivotal studies of liposomal curcumin on symptoms in patients by measuring beneficial efficacy and safety. There are several additional points supporting hippocampal injury as a validated target for PTSD and the therapeutic application of liposomal curcumin: (i) the post-intravenous concentration of liposomal curcumin in the hippocampus emphasizes the drugability of the target[30], (ii) since, curcumin passes the blood brain barrier, and protects the rat striatum and Substantia Nigrum from 6-OHDA toxicity, the chemical drugability is established, and (iii) in order to limit drug toxicity in patients, biomarkers of red blood cell liposomal curcumin toxicity; glutathione, thioredoxin reductase and annexin V, have been identified and can be readily monitored.

The clinical trial: The choice of curcumin for PTSD clinical trials is based upon its mechanisms of action, its distribution across the blood brain barrier and localization in the striata and the hippocampus. The present inventors describe a novel approach to use intravenous liposomal curcumin in a controlled trial design based upon standard Phase I, II, III clinical programs. The working hypothesis is that curcumin acts as an inhibitor of progressive disease and as a mitogen for neural stem cells. Additional biochemical changes monitored during the study. And reflecting levels in the hippocampus include stress induced decreases in 5-HT $_{1A}$mRNA and BDNF protein levels in cerebral spinal fluid. The Phase II trial specifics; dosing schedule, and treatment duration will be based upon a phase I clinical trial. Study size of a comparative phase III trial will depend upon regulatory guidance regarding efficacy of disease modification. Within these trials the present inventors will attempt to measure biomarkers of curcumin-related activity, and imaging of hippocampal neural degeneration and regeneration as outcome measures. The patient population will consist of diagnosed symptomatic patients with an n=300/arm of severely affected PTSD patients. Inclusion criteria will be established behavioral criteria signs of PTSD.

Curcumin improves chronic unpredictable mild stress (CUMS) by inducing low sucrose consumption, lowering serum corticosterone, enhancing adenylyl cyclase (AC) catalytic activity, and cAMP levels in various brain regions, up-regulated mRNA expressions of AC subtypes AC2, AC8, and cAMP response element binding protein (CREB) in the hippocampus, cortex, and hypothalamus of CUMS rats. Rationale for it being an anti-depressant[17].

Curcumin improves the memory ability of Alzheimer's Disease mice (ALCL3 orally and D-galactose IP for 90 days) using the step-through test and prolonged step through latence and inhibits apoptosis induced by AlCl3 in cultured PC12 cells. Mechanism indicated increased BCL-2 but not Bax[18]. Curcumin has antioxidative, antilipofusinogenesic, and anti-aging effects in aging rats[19].

The present invention discloses a major improvement in the clinical management of progressive supranuclear palsy, Alzheimer's disease, Parkinson's disease, Tauopathies and PTSD. The drug crosses the blood brain barrier, localizes in the hippocampus and striata, prevents stress-induced neuronal cell damage, and stimulates neurogenesis and remediation of damaged neural circuits. The change in the therapeutic paradigm of AD, PD, PTSD and other neuronal and neurodegenerative diseases using a chemotherapeutic agent specifically targeted to stress-induced damage of critical neuronal sites as described hereinabove may prove to be a more effective treatment of an unresolved problem.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application No. 20080033055: Method for the Synthesis of Curcumin Analogues.
U.S. Patent Application No. 20090143433: Cocktail for Modulation of Alzheimer's Disease.
U.S. Patent Application No. 20080213246: Supplements for Pain Management.
1. Garcia-Alloza M, Borelli L A, Rozkaine A, Hyman B T, Bacskai B J (2007) Curcumin Labels Amyloid Pathology In Vivo, Disrupts Existing Plaques, and Partially Restores Distorted Neuritis in an Alzheimer Mouse Model. J Neurochem 102(4):1095-1104.

2. Rosi S, Pert C B, Ruff M R, McGann-Gramling and G L Wenk (2005) Chemokine Receptor 5 Antagonist D-Ala-Peptide T-Amide Reduces Microglia and Astrocyte Activation within the Hippocampus in A Neuroinflammatory Rat Model of Alzheimer's Disease. Neuroscience 134:671-676.
3. Kim S J, Son T G, Park H R, Park M, Kim M S, Kim H S, Chung H Y, Mattson M P, Lee J (2008) Curcumin stimulates Proliferation of Embryonic Neural Progenitor Cells and Neurogenesis in the Adult Hippocampus. J Biol Chem 283(21):14497-14505.
4. Anderson P, Morris R, Amaral D, Bliss T and O'Keef J ed. (2007) The Hippocampus Book. Oxford University Press. ISBN 9780195100273.
5. Xu Y, Ku B, Cui L, Li X, Barish P A, Foster T C, and W O Ogle (2007) Curcumin Reverses Impaired Hippocampal Neurogenesis and Increases Serotonin Receptor 1A mRNA and Brain-Derived Neurotrophic Factor Expression in Chronically Stressed Rats. Brain Research 1162:9-18.
6. Ray B, Bisht S, Maitra A, Maitra A, and Lahiri D K (2010) Neuroprotective and Neurorescue Effects of A Novel Polymeric Nanoparticle Formulation of Curcumin (Nanocurc®) in the Neuronal Cell Culture and Animal Model: Implications for Alzheimer's Disease. J. Alzheimer's Disease, in press.
7. Kang S K, Cha S H, Jeon H G (2006) Curcumin-Induced Histone Hypoacetylation Enhances Caspase-3 Dependent Glioma Cell Death and Neurogenesis of Neural Progenitor Cells. Stem Cells Dev. 15(2):165-174.
8. Abel T and R S Zukin (2008) Epigenetic Targets of HDAC Inhibition in Neurodegenerative and Psychiatric Disorders. Curr Opin Pharmacol 8(1):57-64.
9. Lan L, Fadi S, Braiteh F S, and Razelle Kurzrock (2005) Liposome Encapsulated Curcumin, In Vitro and In Vivo Effects on Proliferation, Apoptosis, Signaling and Angiogenesis. Cancer 104:1322-1331.
10. Bisht S, Feldman G, Scheetal S, Ravi, R, Karikari C, Maitra A, Maitra A (2007) Polymeric Nanoparticle Encapsulated Curcumin Nanocurcumin: A Novel Strategy for Human Cancer Therapy. J Nanobiotechnology 5:3.
12. Mukerjee A, and J K Vishwana (2009) Formulation, Characterization and Evaluation of Curcumin Loaded PLGA Nanospheres for Cancer Therapy. J Anticancer Research 29:3867-3876.
13. Li J, Jiang Y, Wen J, Fan G, Wu Y, and C, Zhang (2009) A Rapid and Simple HPLC Method for the Determination of Curcumin in Rat Plasma: Assay Development, Validation and Application to A Pharmacokinetic Study of Curcumin Liposome. Biomed Chromatog 23(11):1201-1207.
14. Rusinek H, Brys M, Glodzik, Switalski R, Tsui W H, Haas F, McGorty K, Chen Q, deLeon M J (2010) Hippocampal Blood Flow in Normal Aging Measured with Arterial Spin Labeling at 3T. Magnetic Resonance in Medicine. [Epub ahead of print].
15. Yadav R S, Sankhwar M L, Shukla R K, Chandra R, Pant A B, Islam F, Khanna V K (2009) Attenuation of Arsenic Neurotoxicity by Curcumin in Rats. Toxicol Appl Pharmacol 240(3):367-376.
16. Atale A, Sabetkasaei M, HaghparastMoghaddam A H, and B Kazeminejad (2010) Neuroprotective Effects of The Polyphenolic Antioxidant Agent, Curcumin, against Homocysteine-Induced Cognitive Impairment and Oxidative Stress in the Rat. Pharmacology, Biochemistry and Behavior 96(4):378-385.
17. Li Y C, Wang F M, Pan Y et al 2009 Antidepressant-like Effects of Curcumin on Serotonergic Receptor-Coupled AC-cAMP Pathway in Chronic Unpredictable Mild Stress of Rats. Prog Neuropsychopharmacol Biol Psychiatry.
18. Pan Rui Qui Sheng, L U Da-xiang, Dong June 2008 Curcumin Improves Learning and Memory Ability and its Neuroprotective Mechanism in Mice. Chinese Medical Journal 121:832-839.
19. Bala K, Tripathy B C, Sharma D 2006 Neuroprotective and Antiaging Effects of Curcumin in Aged Rat Brain Regions.
20. Ronald C. et al Post traumatic stress disorder in the national Comorbidity survey Archives of General Psychiatry, 52(12) 1049-1060.
21. Kulka R A et al Trauma and the Vietnam War Generation: Report of findings from the National Vietnam Veterans Readjustment Study. (New York; Brunner. Mazel, 1990; ISBN 0-87630-573-7).
22. Journal of Traumatic Stress, February 2010.
23. Ying Xu, Baoshan K U, Li Cui et al. 2007 Curcumin reverses impaired hippocampal neurogenesis and increases serotonin receptor 1A mRNA and brain-derived neurotrophic factor expression in chronically stressed rats. Brain Research 1162:9-18.
24. Anisman H et al. 1979 Escape performance after inescapable shock in selectively bred lines of mice: response maintenance and catecholamine activity. J Comp Physiol Psychol 93(2):229-241.
25. Sack W H et al 1995. Posttraumatic stress disorder across two generations of Cambodian refugees. J Am Adad Child Adolesc Psychiatry 34(9):1160-1166.
26. Stein M B et al 2002 Genetic and environmental influences on trauma exposure and post traumatic stress disorder: a twin study. Am J Psychiatry 159(10) 1675-1681.
27. Segman R H et al 2002. Association between the dopamine transporter gene and post traumatic stress disorder. Mol Psychiatry 7(8):903-907.
28. Segman R H 2005. Peripheral blood mononuclear cell gene expression profiles identify emergent post-traumatic stress disorder among trauma survivors.
29. Pitman R K and Delahanty D L 2005. Conceptually driven pharmacologic approaches to acute trauma CNS Spectr 10(2):99-106.
30. Chiu S, Lui E, Majeed M, Vishwanatha J K, Ranjan A, Maitra A, Dipanker P, Smith J A, Helson L. 2010. Intravenous Curcumin Distribution in the Rat Brain. J Anticancer Research, 31(3):3-7.

What is claimed is:

1. A method for ameliorating symptoms and/or treating one or more neurodegenerative diseases, in a subject comprising the steps of:
    identifying the subject in need of ameliorating symptoms and/or treatment against one or more neurodegenerative diseases; and
    administering intravenously a therapeutically effective amount of a pharmaceutical composition that ameliorates the symptoms or that treats a neurodegenerative disease comprising a curcuminoid, wherein the curcuminoid comprises curcumin dissolved or dispersed in a suitable aqueous or non-aqueous medium, wherein the curcumin is a poly-lactic-glycolic-acid (PLGA)-curcumin conjugate enclosed in one or more liposomes that cross the blood brain barrier and concentrate in the hippocampus and the striatum, the size being about 100 nanometer (nm), wherein the curcumin has been synthesized to a 99.2% purity and reaches the hippocampus at a concentration that is at least half the concentration in plasma at two hours, wherein the intravenous liposomal curcumin is administered at 20 mg/kg.

2. The method of claim 1, further comprising the step of monitoring the efficacy of the amelioration of the symptoms or the treatment of the neurodegenerative diseases, in the subject.

3. The method of claim 1, wherein the liposomes comprise a lipid or a phospholipid wall.

4. The method of claim 3, wherein the lipids or the phospholipids are selected from the group consisting of phosphatidylcholine, lysolecithin, lysophosphatidylethanol-amine, phosphatidylserine, phosphatidylinositol, sphingomyelin, phosphatidylethanolamine, cardiolipin, phosphatidic acid, cerebrosides, dicetylphosphate, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerol succinate.

5. The method of claim 1, wherein the composition further comprises a biodegradable polymer is selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), copolymers, terpolymers, and combinations or mixtures thereof.

6. The method of claim 1, wherein the therapeutically effective amount comprises 50 nM/kg of body weight of the subject.

7. The method of claim 1, wherein the pharmaceutical composition is optionally administered along with related co-factors, proteins, antibodies, pain medications, and other pharmaceutically active agents.

8. The method of claim 7, wherein the pharmaceutically active agents comprise a serotonin reuptake inhibitor, sertraline or, paroxetine.

9. A method of ameliorating symptoms and/or treating, Parkinson's disease (PD), in a subject comprising the steps of:
identifying the subject in need of amelioration and/or treatment against Parkinson's disease (PD); and
administering intravenously a therapeutically effective amount of a pharmaceutical composition that ameliorates the symptoms or that treats the PD comprising a curcuminoid, wherein the curcuminoid comprises curcumin and is a poly-lactic-glycolic-acid (PLGA)-curcumin conjugate enclosed in one or more liposomes sized to cross the blood brain barrier and concentrate in the hippocampus and the striatum, the size being about 100 nanometer (nm), wherein the curcumin has been synthesized to a 99.2% purity and a concentration level of curcumin that reaches the hippocampus at a concentration that is at least half the concentration in plasma at two hours, wherein the intravenous liposomal curcumin is administered at 20 mg/kg.

10. The method of claim 9, further comprising the step of monitoring the efficacy of the amelioration of the symptoms or the treatment by improvements in memory, cognition, learning, speech, one or more motor skills, mood, behavior or combinations thereof in the subject.

11. The method of claim 9, wherein the liposomes comprise a lipid or a phospholipid wall.

12. The method of claim 11, wherein the lipids or the phospholipids are selected from the group consisting of phosphatidylcholine, lysolecithin, lysophosphatidylethanolamine, phosphatidylserine, phosphatidylinositol, sphingomyelin, phosphatidylethanolamine, cardiolipin, phosphatidic acid, cerebrosides, dicetylphosphate, and dipalmitoyl-phosphatidylglycerol, stearylamine, dodecylamine, hexadecylamine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerol succinate.

13. The method of claim 9, wherein the therapeutically effective amount comprises 50 nM/kg of body weight of the subject.

14. The method of claim 9, wherein the pharmaceutical composition is optionally administered along with related co-factors, proteins, antibodies, pain medications, and other pharmaceutically active agents.

15. The method of claim 14, wherein the one or more pharmaceutically active agents are selected from the group consisting of serotonin reuptake inhibitors sertraline, paroxetine, L-dopa, Carbidopa, benserazide, Tolcapone, dopamine agonists bromocriptine, pergolide, pramipexole, ropinirole, piribedil, cabergoline, apomorphine, lisuride, MAO inhibitors, selegiline, and rasagiline.

* * * * *